(12) United States Patent
Kassab et al.

(10) Patent No.: US 8,211,084 B2
(45) Date of Patent: Jul. 3, 2012

(54) DEVICES, SYSTEMS, AND METHODS FOR ACCESSING THE EPICARDIAL SURFACE OF THE HEART

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 174 days.

(21) Appl. No.: 12/596,964

(22) PCT Filed: Feb. 5, 2008

(86) PCT No.: PCT/US2008/053061
§ 371 (c)(1),
(2), (4) Date: Mar. 10, 2010

(87) PCT Pub. No.: WO2008/134104
PCT Pub. Date: Nov. 6, 2008

(65) Prior Publication Data
US 2011/0130744 A1 Jun. 2, 2011

Related U.S. Application Data

(60) Provisional application No. 60/914,452, filed on Apr. 27, 2007, provisional application No. 60/817,421, filed on Jun. 30, 2006.

(30) Foreign Application Priority Data

Jun. 29, 2007 (WO) ................ PCT/US2007/015207

(51) Int. Cl.
*A61M 1/00* (2006.01)
*A61M 5/00* (2006.01)
*A61B 19/00* (2006.01)
*A61B 17/03* (2006.01)

(52) U.S. Cl. .................... 604/508; 606/129; 606/213
(58) Field of Classification Search .................. 604/508; 606/213, 129
See application file for complete search history.

(56) References Cited

U.S. PATENT DOCUMENTS

| | | | |
|---|---|---|---|
| 3,583,404 A | 6/1971 | McWhorter | |
| 3,630,207 A | 12/1971 | Kahn et al. | |
| 4,946,457 A | 8/1990 | Elliott | |
| 4,991,578 A | 2/1991 | Cohen | |
| 5,195,968 A | 3/1993 | Lundquist et al. | |
| 5,292,332 A | 3/1994 | Lee | |
| 5,715,817 A | 2/1998 | Stevens-Wright et al. | |
| 5,972,013 A * | 10/1999 | Schmidt | 606/185 |
| 6,113,611 A | 9/2000 | Allen et al. | |
| 6,200,303 B1 | 3/2001 | Verrior et al. | |

(Continued)

OTHER PUBLICATIONS

Uchida et al, "Angiogenic therapy of acute myocardial infarction by intrapericardial injection of . . . " American Heart Journal, vol. 130, No. 6, pp. 1182-1188 (Dec. 1995).

(Continued)

*Primary Examiner* — Jackie Ho
*Assistant Examiner* — Michael J Anderson
(74) *Attorney, Agent, or Firm* — Ice Miller LLP

(57) ABSTRACT

Devices, systems, and methods for accessing the internal and external tissues of the heart are disclosed. At least some of the embodiments disclosed herein provide access to the external surface of the heart through the pericardial space for localized delivery of leads to the heart tissue. In addition, various disclosed embodiments provide devices, systems, and methods for closing a hole in cardiac tissue.

25 Claims, 21 Drawing Sheets

U.S. PATENT DOCUMENTS

| | | | |
|---|---|---|---|
| 6,338,345 | B1 | 1/2002 | Johnson et al. |
| 6,500,167 | B1 | 12/2002 | Webster, Jr. |
| 6,595,982 | B2 | 7/2003 | Sekino et al. |
| 6,613,062 | B1 * | 9/2003 | Leckrone et al. ............ 606/167 |
| 6,626,930 | B1 | 9/2003 | Allen et al. |
| 6,663,633 | B1 | 12/2003 | Pierson, III |
| 6,692,458 | B2 | 2/2004 | Forman et al. |
| 6,776,784 | B2 | 8/2004 | Ginn |
| 6,837,893 | B2 | 1/2005 | Miller |
| 6,890,295 | B2 | 5/2005 | Michels |
| 6,918,890 | B2 | 7/2005 | Schmidt |
| 6,991,616 | B2 | 1/2006 | Bencini et al. |
| 7,029,468 | B2 | 4/2006 | Honebrink |
| 7,081,125 | B2 | 7/2006 | Edwards et al. |
| 7,326,231 | B2 | 2/2008 | Phillips et al. |
| 7,842,068 | B2 | 11/2010 | Ginn |
| 7,931,628 | B2 | 4/2011 | Zhu et al. |
| 7,942,897 | B2 | 5/2011 | Lafontaine |
| 2002/0072768 | A1 | 6/2002 | Ginn |
| 2002/0091354 | A1 * | 7/2002 | Navia et al. ............... 604/96.01 |
| 2002/0165561 | A1 | 11/2002 | Ainsworth |
| 2002/0168317 | A1 * | 11/2002 | Daighighian et al. ....... 424/1.11 |
| 2003/0009145 | A1 * | 1/2003 | Struijker-Boudier et al. 604/500 |
| 2003/0109852 | A1 | 6/2003 | Peterson et al. |
| 2003/0225420 | A1 | 12/2003 | Wardle |
| 2004/0010216 | A1 | 1/2004 | Zhu et al. |
| 2004/0018228 | A1 | 1/2004 | Fischell et al. |
| 2004/0086479 | A1 | 5/2004 | Grinstaff et al. |
| 2004/0087938 | A1 * | 5/2004 | Leckrone et al. ............... 606/41 |
| 2004/0230131 | A1 | 11/2004 | Kassab et al. |
| 2005/0113760 | A1 * | 5/2005 | Chachques et al. ........... 604/174 |
| 2005/0256450 | A1 | 11/2005 | Palasis et al. |
| 2005/0261673 | A1 * | 11/2005 | Bonner et al. ................. 606/41 |
| 2006/0106442 | A1 | 5/2006 | Richardson et al. |
| 2006/0207612 | A1 * | 9/2006 | Jackson et al. ............... 128/860 |
| 2006/0217764 | A1 | 9/2006 | Abbott et al. |
| 2006/0240113 | A1 * | 10/2006 | Hunter et al. ................. 424/489 |
| 2007/0010708 | A1 * | 1/2007 | Ness ........................... 600/115 |

OTHER PUBLICATIONS

International Searching Authority, International Search Report, mailed Sep. 11, 2008 (PCT/US2007/015207).

International Searching Authority, Written Opinion of the International Searching Authority, mailed Sep. 11, 2008 (PCT/US2007/015207).

Huang, Engineering RGC-Modified Liposomes for Targeted Drug Delivery to Activated Platelets. PhD Thesis, Case Western Reserve University, Aug. 2006.

International Searching Authority, International Search Report, mailed Oct. 1, 2008 (PCT/US08/53061).

International Searching Authority, Written Opinion of the International Searching Authority, mailed Oct. 1, 2008 (PCT/US08/53061).

* cited by examiner

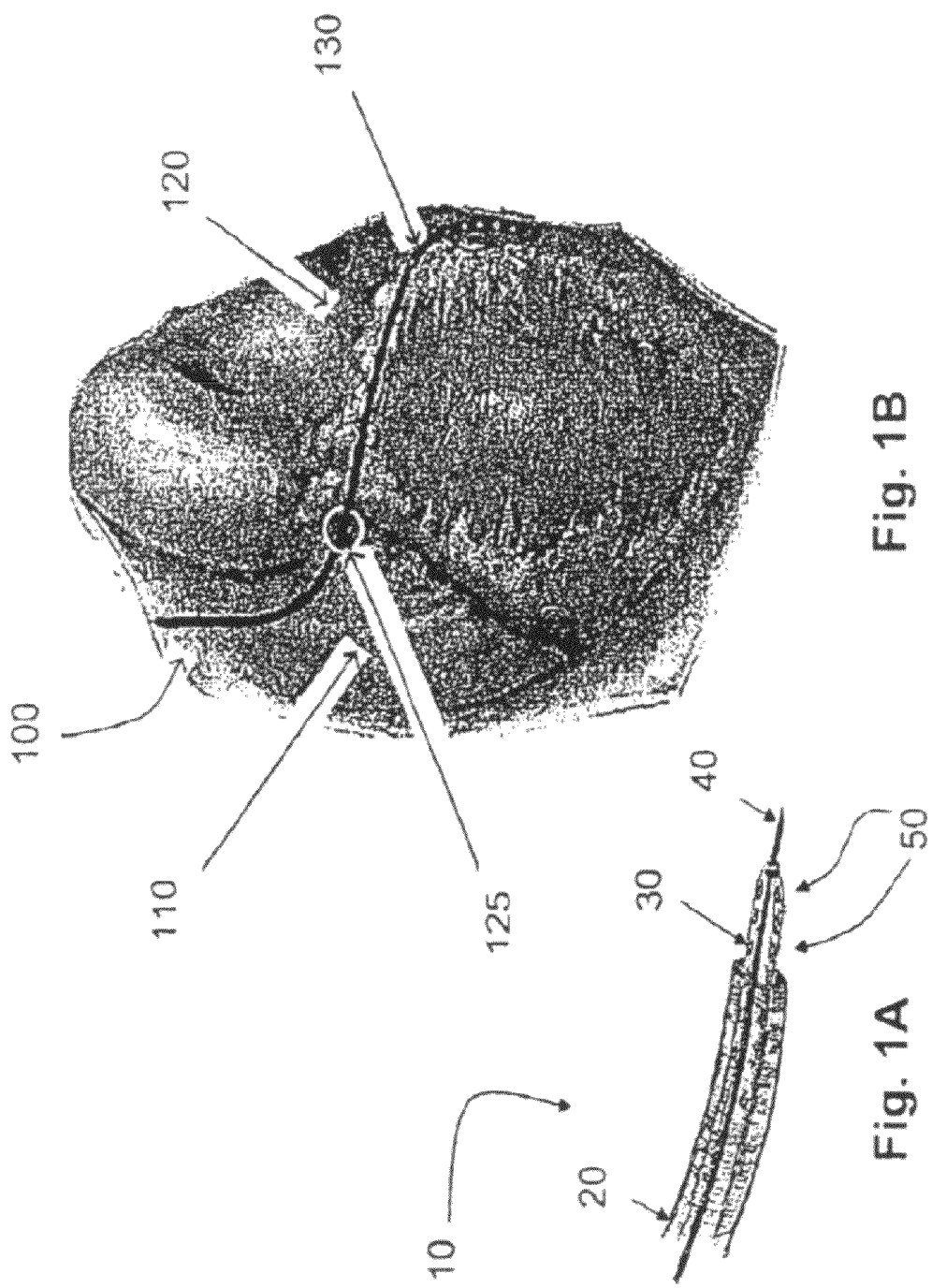

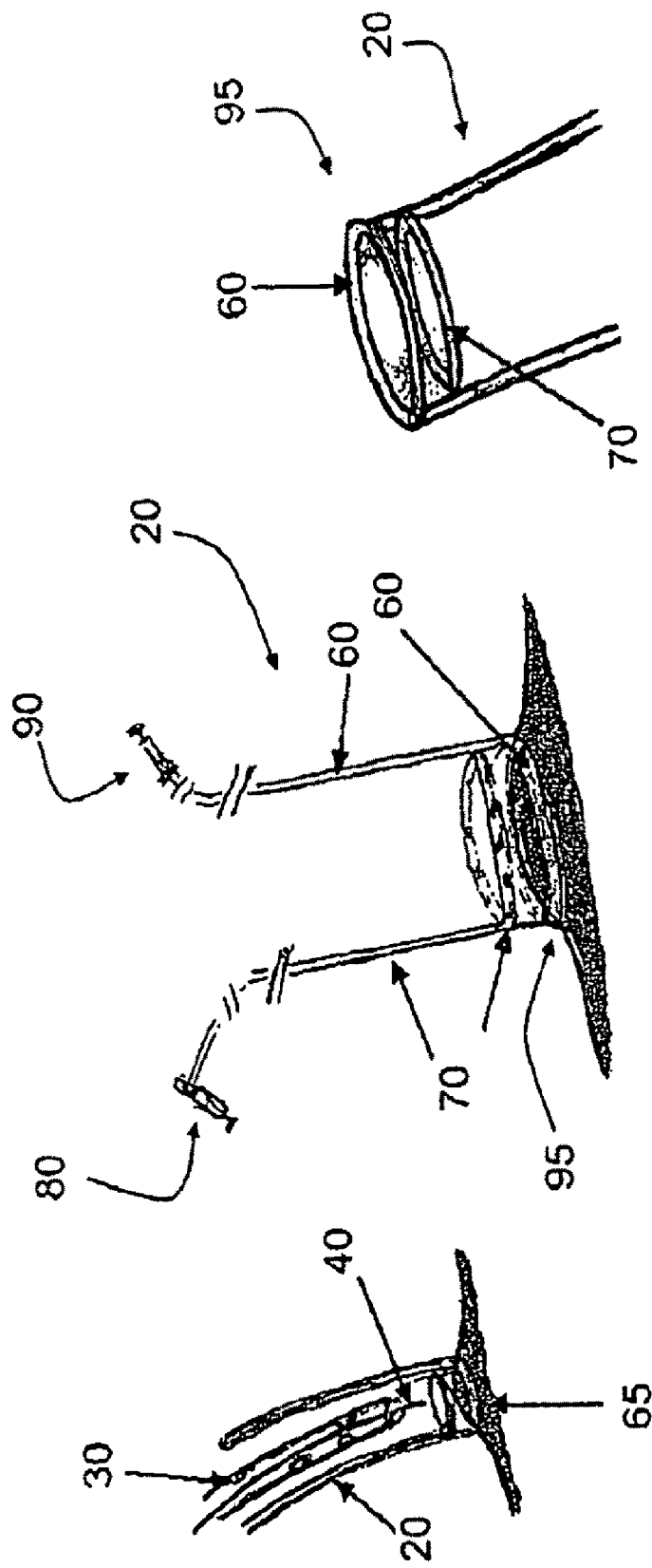

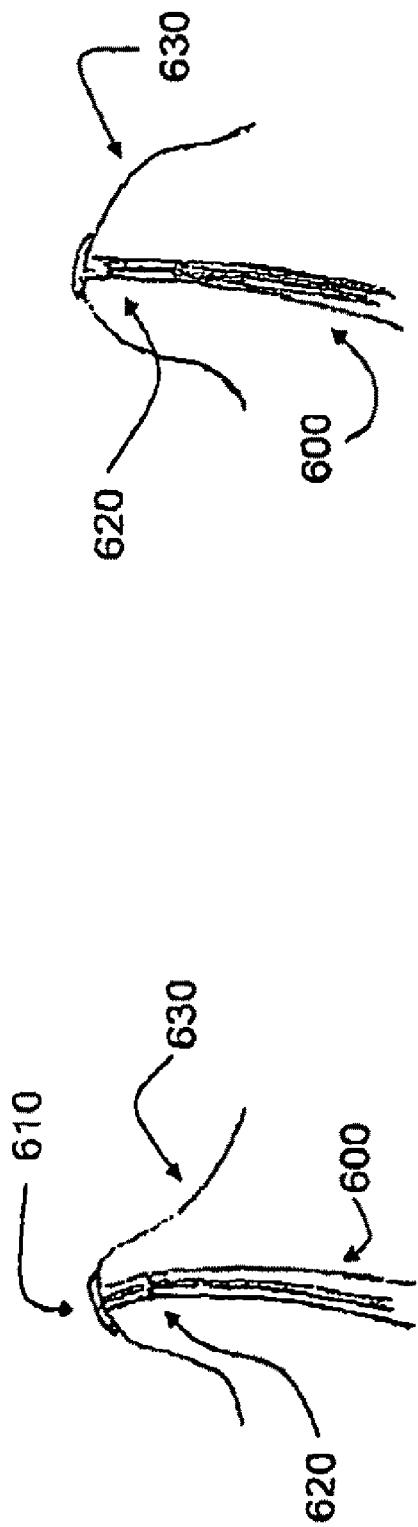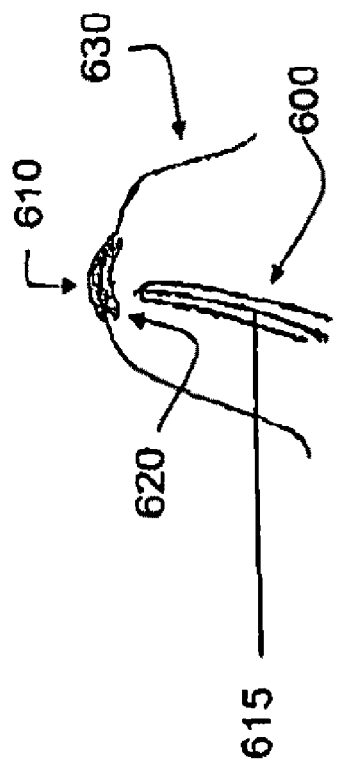

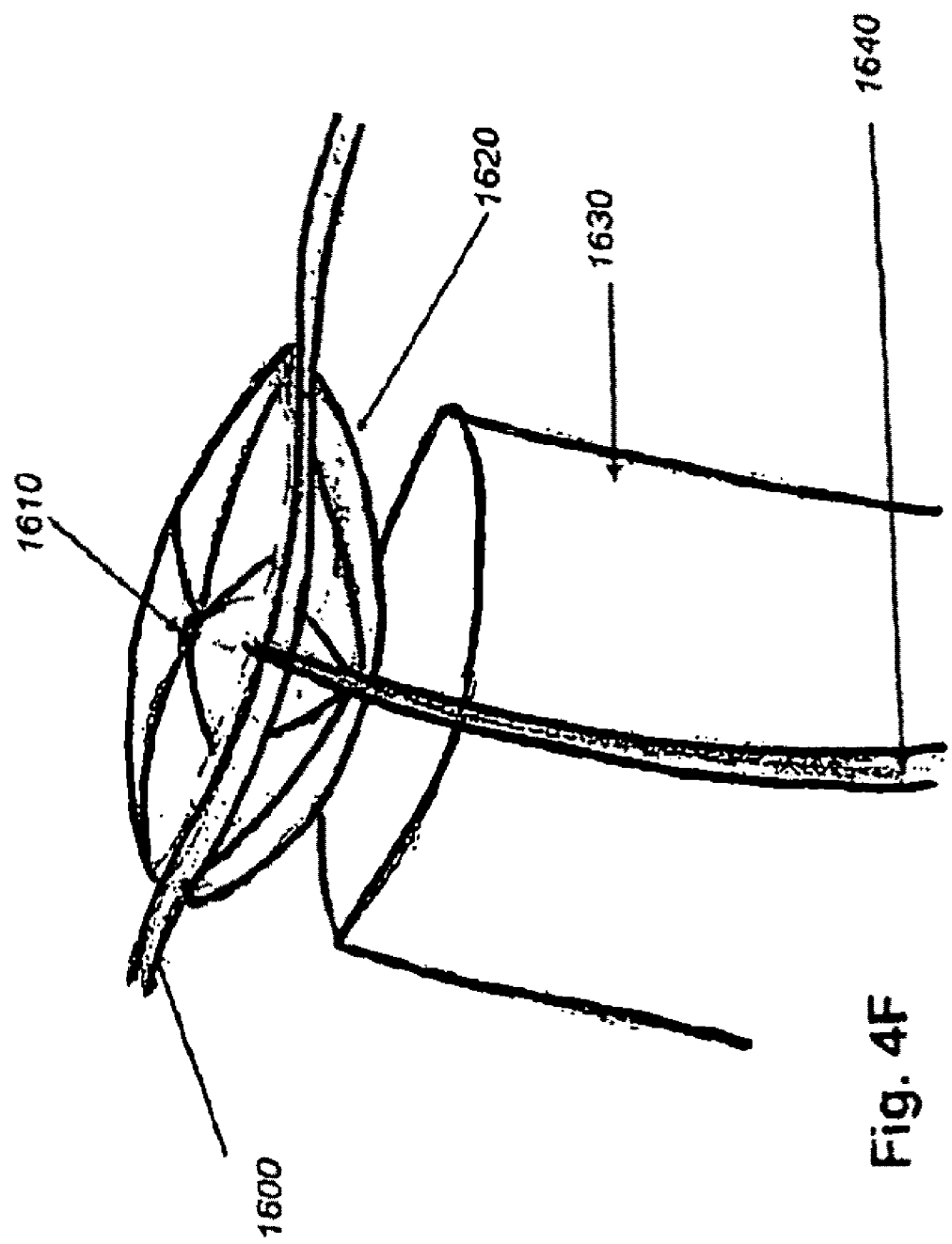

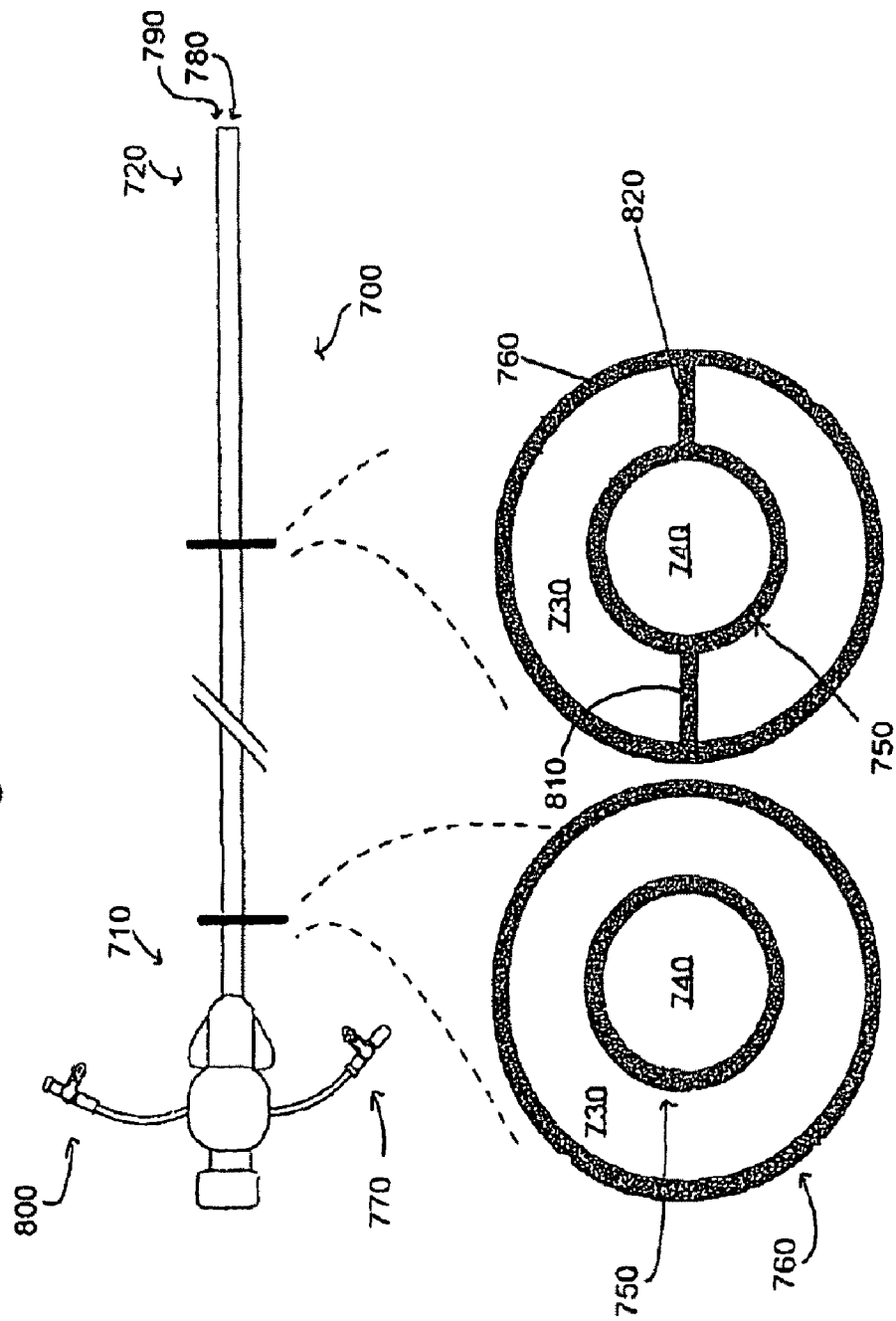

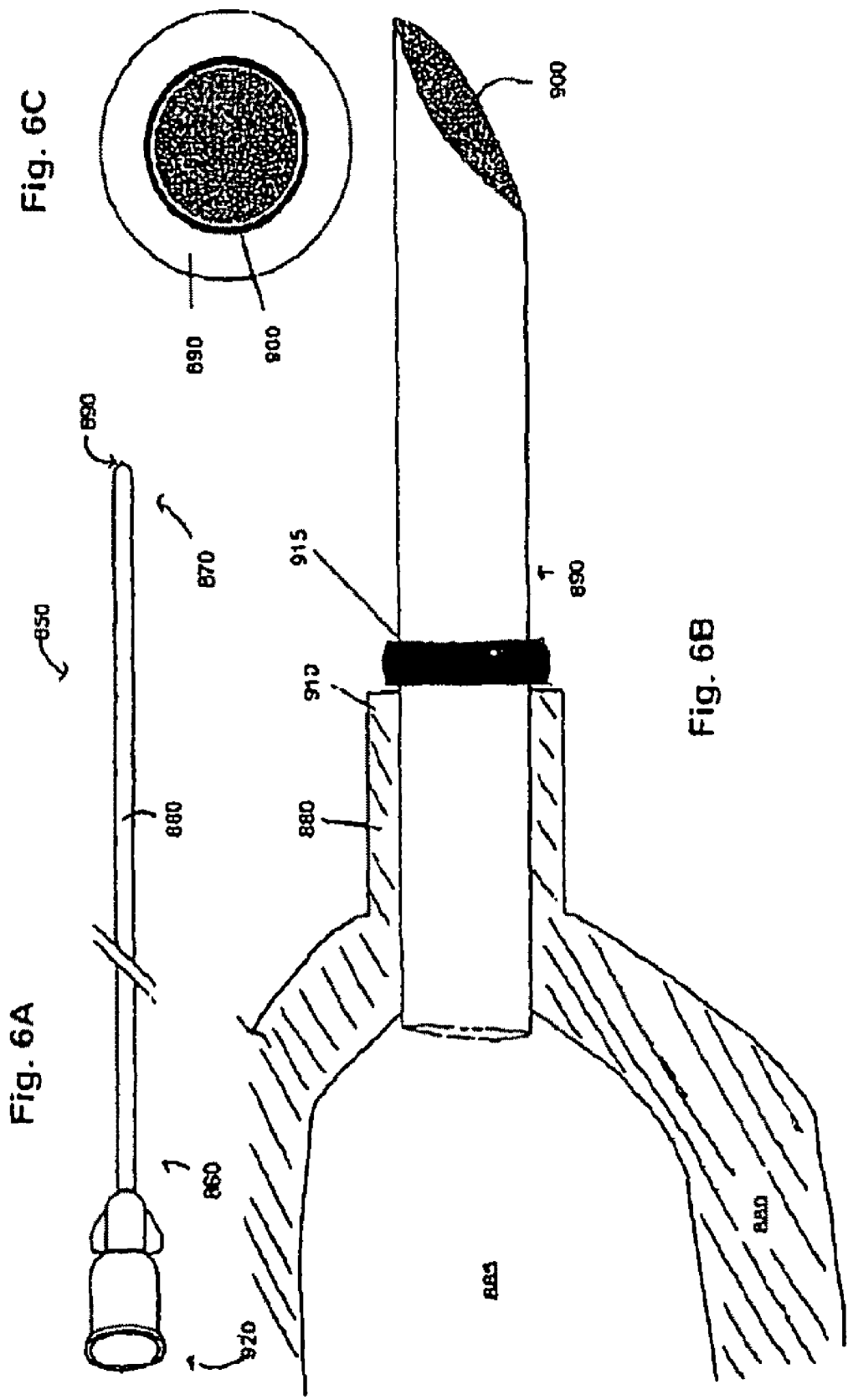

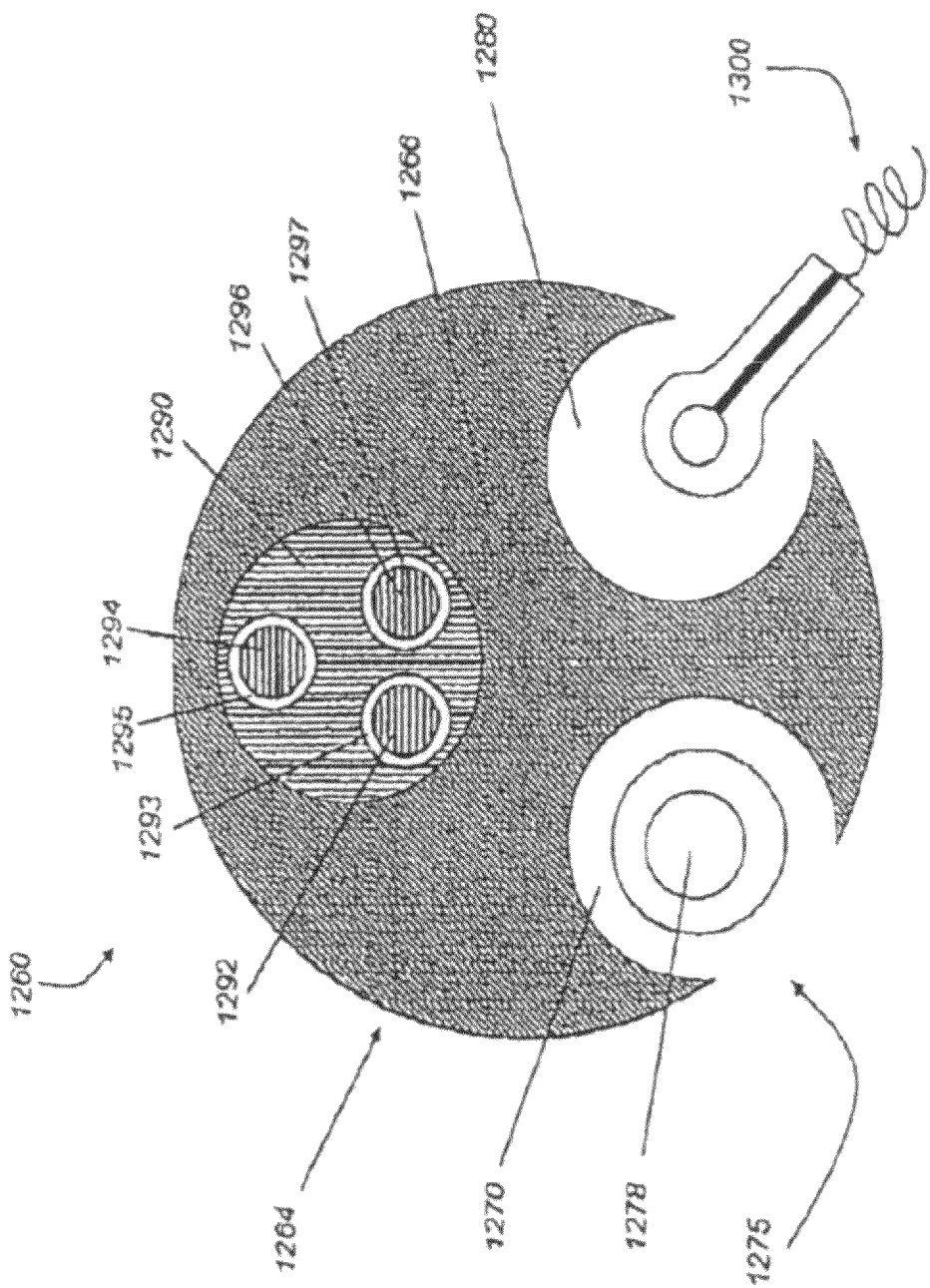

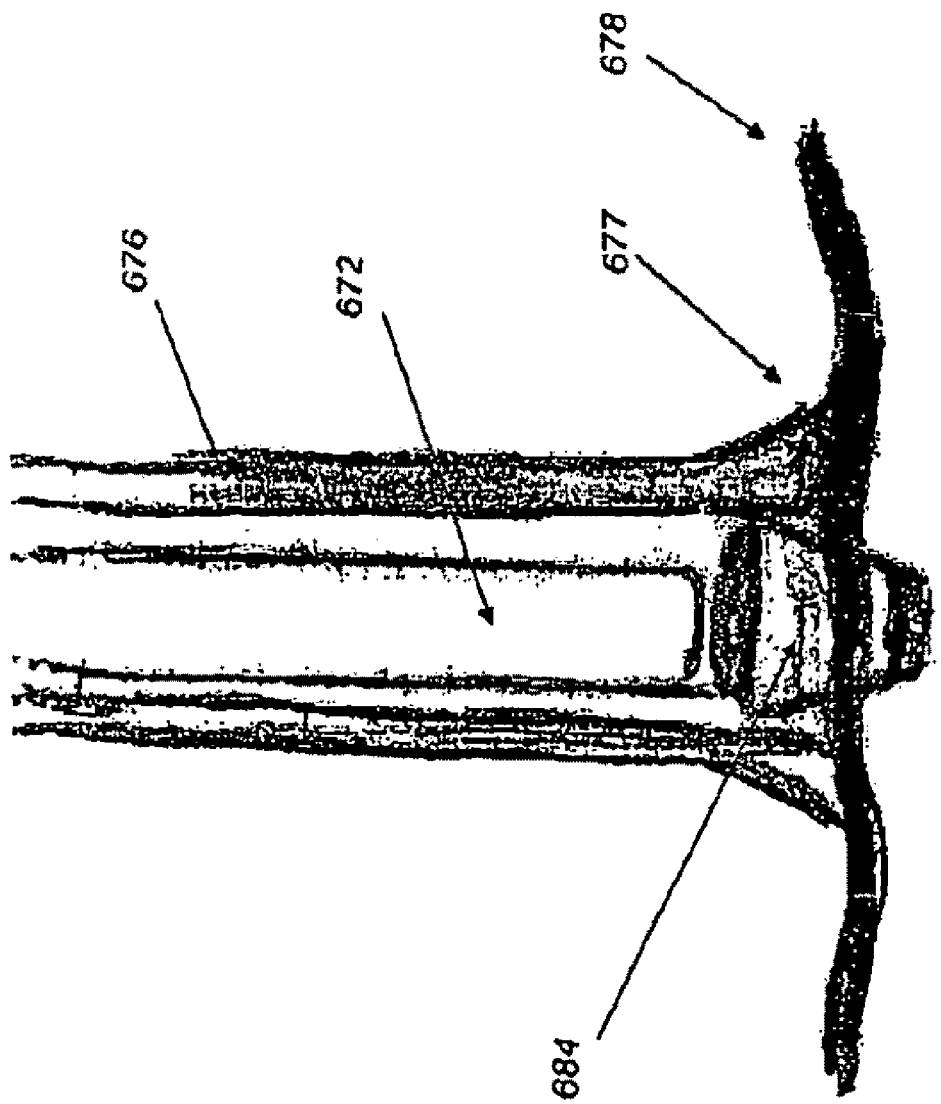

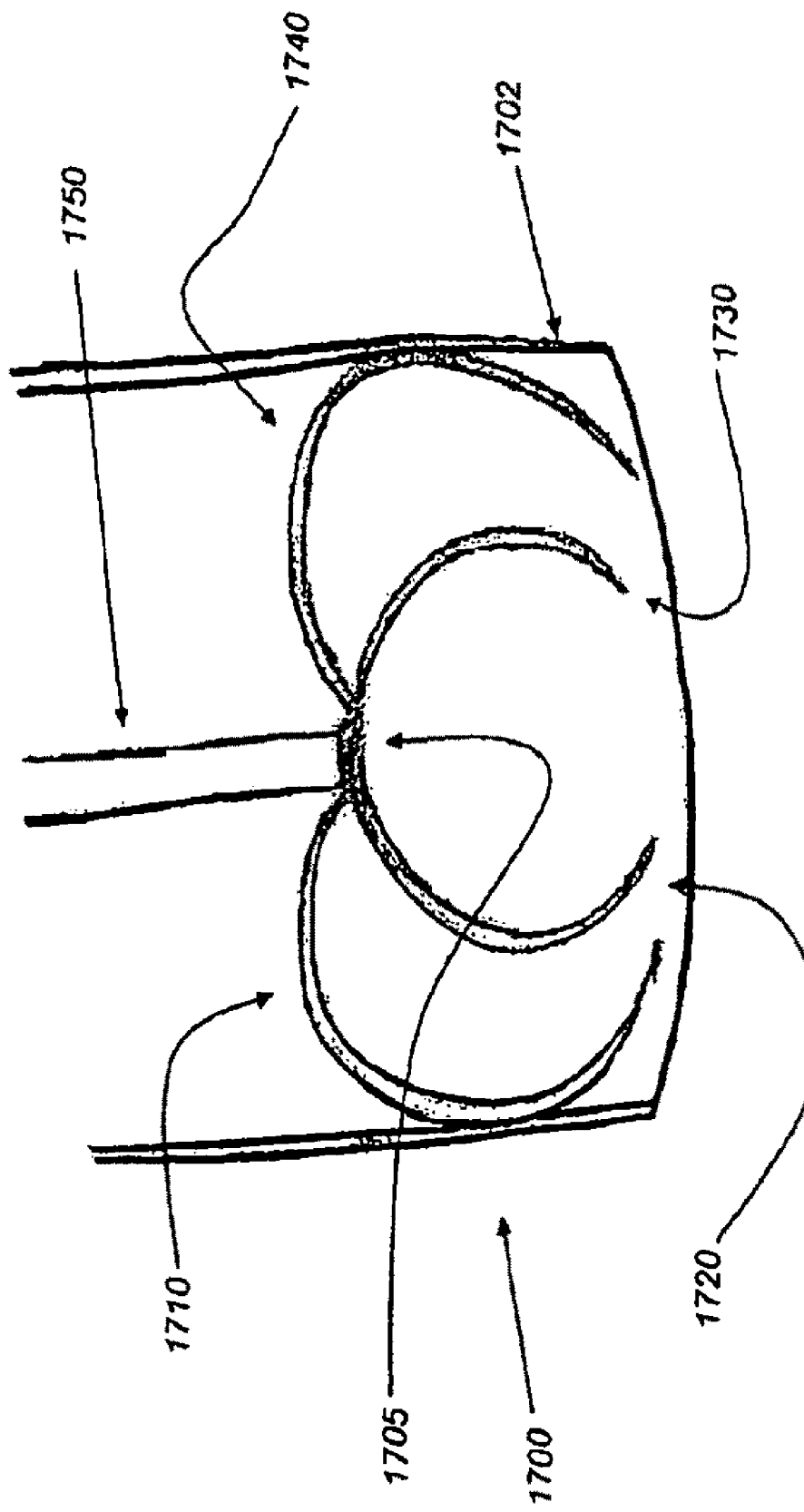

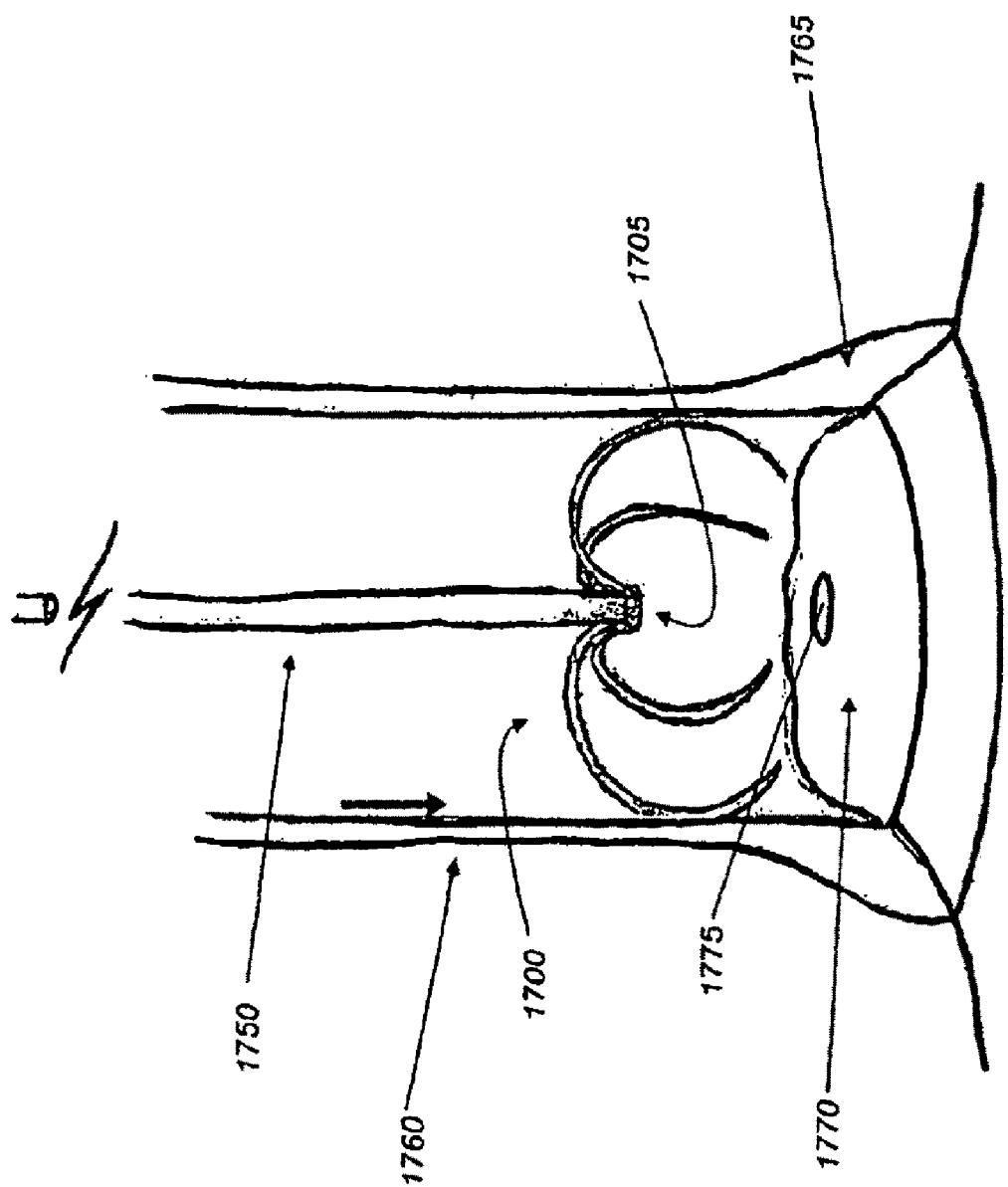

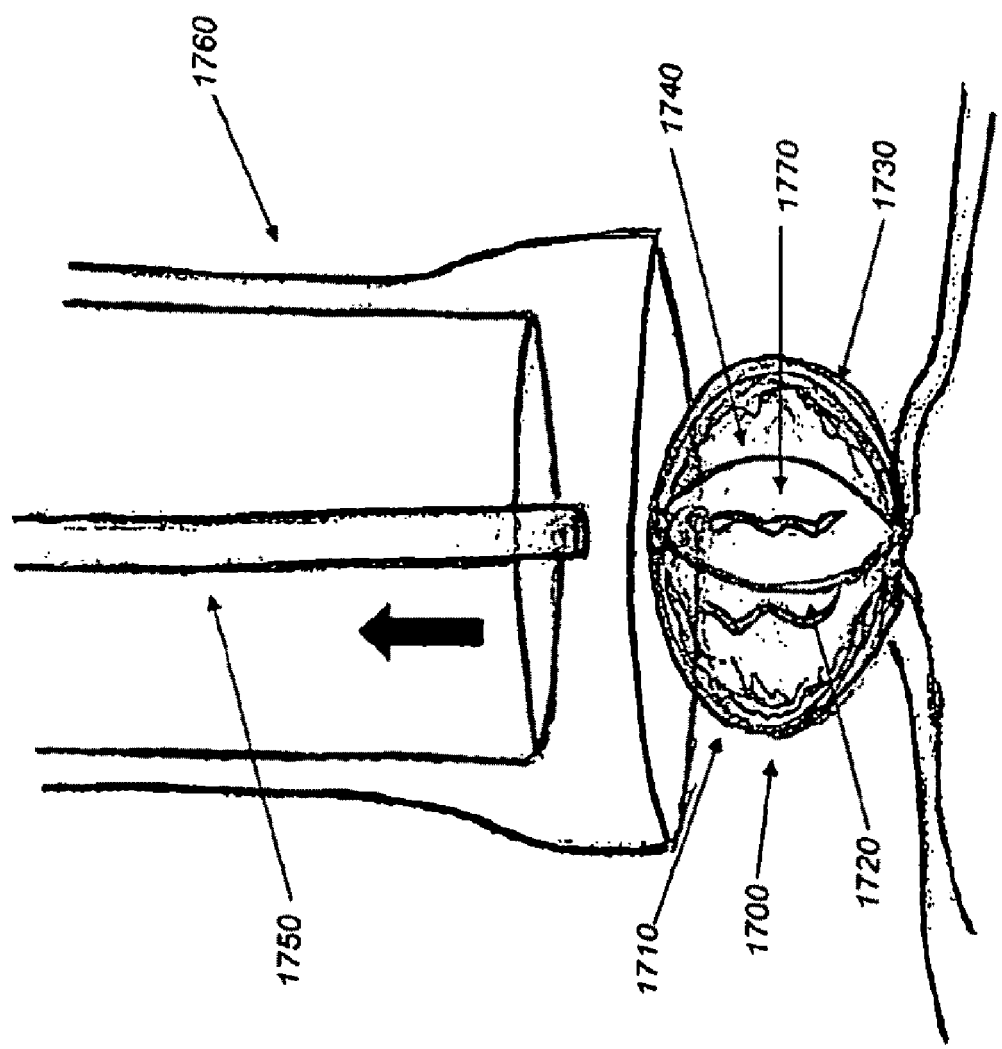

DEVICES, SYSTEMS, AND METHODS FOR ACCESSING THE EPICARDIAL SURFACE OF THE HEART

PRIORITY

The present application is related to, and claims the priority benefit of, International Patent Application Serial No. PCT/US2008/053061, filed Feb. 5, 2008, which is related to, claims the priority benefit of, and in at least some designated countries should be considered a continuation-in-part application of, International Patent Application No. PCT/US2007/015207, filed Jun. 29, 2007, which is related to, and claims the priority benefit of, U.S. Provisional Patent Application Ser. No. 60/914,452, filed Apr. 27, 2007, and U.S. Provisional Patent Application Ser. No. 60/817,421, filed Jun. 30, 2006. The present application also claims the priority benefit of International Patent Application No. PCT/US2007/015207, filed Jun. 29, 2007, and U.S. Provisional Patent Application Ser. No. 60/914,452, filed Apr. 27, 2007. The contents of each of these applications are hereby incorporated by reference in their entirety into this disclosure.

BACKGROUND

Ischemic heart disease, or coronary heart disease, kills more Americans per year than any other single cause. In 2004, one in every five deaths in the United States resulted from ischemic heart disease. Indeed, the disease has had a profound impact worldwide. If left untreated, ischemic heart disease can lead to chronic heart failure, which can be defined as a significant decrease in the heart's ability to pump blood. Chronic heart failure is often treated with drug therapy.

Ischemic heart disease is generally characterized by a diminished flow of blood to the myocardium and is also often treated using drug therapy. Although many of the available drugs may be administered systemically, local drug delivery ("LDD") directly to the heart can result in higher local drug concentrations with fewer systemic side effects, thereby leading to improved therapeutic outcomes.

Cardiac drugs may be delivered locally via catheter passing through the blood vessels to the inside of the heart. However, endoluminal drug delivery has several shortcomings, such as: (1) inconsistent delivery, (2) low efficiency of localization, and (3) relatively rapid washout into the circulation.

To overcome such shortcomings, drugs may be delivered directly into the pericardial space, which surrounds the external surface of the heart. The pericardial space is a cavity formed between the heart and the relatively stiff pericardial sac that encases the heart. Although the pericardial space is usually quite small because the pericardial sac and the heart are in such close contact, a catheter may be used to inject a drug into the pericardial space for local administration to the myocardial and coronary tissues. Drug delivery methods that supply the agent to the heart via the pericardial space offer several advantages over endoluminal delivery, including: (1) enhanced consistency and (2) prolonged exposure of the drug to the cardiac tissue.

In current practice, drugs are delivered into the pericardial space either by the percutaneous transventricular method or by the transthoracic approach. The percutaneous transventricular method involves the controlled penetration of a catheter through the ventricular myocardium to the pericardial space. The transthoracic approach involves accessing the pericardial space from outside the heart using a sheathed needle with a suction tip to grasp the pericardium, pulling it away from the myocardium to enlarge the pericardial space, and injecting the drug into the space with the needle.

For some patients with chronic heart failure, cardiac resynchronization therapy ("CRT") can be used in addition to drug therapy to improve heart function. Such patients generally have an abnormality in conduction that causes the right and left ventricles to beat (i.e., begin systole) at slightly different times, which further decreases the heart's already-limited function. CRT helps to correct this problem of dyssynchrony by resynchronizing the ventricles, thereby leading to improved heart function. The therapy involves the use of an implantable device that helps control the pacing of at least one of the ventricles through the placement of electrical leads onto specified areas of the heart. Small electrical signals are then delivered to the heart through the leads, causing the right and left ventricles to beat simultaneously.

Like the local delivery of drugs to the heart, the placement of CRT leads on the heart can be challenging, particularly when the target placement site is the left ventricle. Leads can be placed using a transvenous approach through the coronary sinus, by surgical placement at the epicardium, or by using an endocardial approach. Problems with these methods of lead placement can include placement at an improper location (including inadvertent placement at or near scar tissue, which does not respond to the electrical signals), dissection or perforation of the coronary sinus or cardiac vein during placement, extended fluoroscopic exposure (and the associated radiation risks) during placement, dislodgement of the lead after placement, and long and unpredictable times required for placement (ranging from about 30 minutes to several hours).

Clinically, the only approved non-surgical means for accessing the pericardial space include the subxiphoid and the ultrasound-guided apical and parasternal needle catheter techniques, and each methods involves a transthoracic approach. In the subxiphoid method, a sheathed needle with a suction tip is advanced from a subxiphoid position into the mediastinum under fluoroscopic guidance. The catheter is positioned onto the anterior outer surface of the pericardial sac, and the suction tip is used to grasp the pericardium and pull it away from the heart tissue, thereby creating additional clearance between the pericardial sac and the heart. The additional clearance tends to decrease the likelihood that the myocardium will be inadvertently punctured when the pericardial sac is pierced.

Although this technique works well in the normal heart, there are major limitations in diseased or dilated hearts—the very hearts for which drug delivery and CRT lead placement are most needed. When the heart is enlarged, the pericardial space is significantly smaller and the risk of puncturing the right ventricle or other cardiac structures is increased. Additionally, because the pericardium is a very stiff membrane, the suction on the pericardium provides little deformation of the pericardium and, therefore, very little clearance of the pericardium from the heart.

Thus, there is need for an efficient, easy to use, and relatively inexpensive technique that can be used to access the heart for local delivery of therapeutic and diagnostic substances, as well as of CRT leads and other types of leads.

BRIEF SUMMARY

Disclosed herein are devices, systems, and methods for accessing the internal and external tissues of the heart. At least some of the disclosed embodiments provide access to the external surface of the heart through the pericardial space for localized delivery of leads to the heart tissue. In addition, various disclosed embodiments provide devices, systems, and methods for closing a hole or wound in cardiac tissue.

For example, disclosed herein is a system for use with a vacuum source for placing a lead into a tissue of a heart, comprising an engagement catheter comprising a proximal end, a distal end, and first and second lumens extending between the proximal end and the distal end; a delivery catheter comprising an elongated tube having a wall and a first lumen, wherein the delivery catheter is configured such that the delivery catheter is capable of at least partial insertion into the second lumen of the engagement catheter; a lead having a tip at a distal end, the lead configured for at least partial insertion into the first lumen of the delivery catheter; and a vacuum port located at the proximal end of the engagement catheter, the vacuum port being operatively connected to the first lumen of the engagement catheter and capable of operative connection to the vacuum source; wherein the first lumen of the engagement catheter includes a suction port located at or near the distal end of the engagement catheter, the suction port being configured to removably attach to a targeted tissue on the interior of a wall of the heart, such that the suction port is capable of forming a reversible seal with the targeted tissue when the vacuum source is operatively attached to the vacuum port, and wherein the system is capable of enlarging a pericardial space between the targeted tissue and a pericardial sac that surrounds the heart by retracting the targeted tissue away from the pericardial sac. In at least some embodiments, the first lumen of the delivery catheter extends from approximately the proximal end of the tube to or near the distal end of the tube, the first lumen of the delivery catheter having a bend, relative to the tube, at or near the distal end of the tube and an outlet through the wall of the tube at or near the distal end of the tube. In addition, the bend of the first lumen of the delivery catheter may form an angle that is approximately 90-degrees.

Certain disclosed embodiments of the delivery catheter disclosed herein may further comprise a second lumen extending from approximately the proximal end of the tube to or near the distal end of the tube, the second lumen of the delivery catheter having a bend, relative to the tube, at or near the distal end of the tube and an outlet through the wall of the tube at or near the distal end of the tube. The bend of the second lumen of the delivery catheter may form an angle that is approximately 90-degrees.

In certain embodiments, the lead comprises a pacing lead, and the tip of the pacing lead has a substantially screw-like shape.

The delivery catheter may further comprise a steering channel extending from a proximal end of the tube to a distal end of the tube and a steering wire system at least partially located in the steering channel. The steering wire system may comprise a first steering wire, a second steering wire, and a controller, each of the first and second steering wires being attached to the wall of the tube within the steering channel and the controller being attached to a proximal end of each of the first and second steering wires. The controller of the steering wire system may comprise a first handle attached to the proximal end of the first steering wire and a second handle attached to the proximal end of the second steering wire.

In at least some embodiments, the controller of the steering wire system comprises a torque system having a first rotatable spool capable of collecting and dispensing the first steering wire and a second rotatable spool capable of collecting and dispensing the second steering wire.

In some embodiments, the steering wire system further comprises a third steering wire; the first steering wire is attached to the wall of the tube within the steering channel at the distal end of the tube, the attachment between the first steering wire and the wall forming a first attachment point; the second steering wire is attached to the wall of the tube within the steering channel at the distal end of the tube, the attachment between the second steering wire and the wall forming a second attachment point; the third steering wire is attached to the wall of the tube within the steering channel at the distal end of the tube, the attachment between the third steering wire and the wall forming a third attachment point; and the third attachment point is closer to the proximal end of the tube than is the first attachment point or the second attachment point.

In some embodiments, the delivery catheter further comprises a handle at or near the proximal end of the tube; and the controller of the steering wire system is attached to the handle.

Also disclosed herein is a delivery catheter for use in accessing a pericardial space surrounding the external surface of a heart, comprising an elongated tube comprising a wall extending from a proximal end of the tube to a distal end of the tube, a first lumen, and a steering channel extending from a proximal end of the tube to a distal end of the tube, the steering channel forming an orifice at the distal end of the tube; and a steering wire system at least partially located in the steering channel, the steering wire system comprising at least two steering wires attached to the wall of the tube within the steering channel and a controller attached to a proximal end of each of the at least two steering wires; wherein the first lumen extends from approximately the proximal end of the tube to or near the distal end of the tube, the first lumen having a bend, relative to the tube, at or near the distal end of the tube and an outlet through the wall of the tube at or near the distal end of the tube. In at least some embodiments, the steering channel of the tube and the orifice of the tube are sized for insertion over an elongated guide wire such that the elongated guide wire is inserted through the orifice and into the steering channel. Certain embodiments further comprise a pacing lead sized for delivery through the outlet of the first lumen.

In certain embodiments, the at least two steering wires comprise a first steering wire and a second steering wire; and the controller of the steering wire system comprises a first handle attached to the proximal end of the first steering wire and a second handle attached to the proximal end of the second steering wire. The controller of the steering wire system may comprise a torque system having a first rotatable spool capable of collecting and dispensing the first steering wire and a second rotatable spool capable of collecting and dispensing the second steering wire. The first rotatable spool may be attached to a first rotatable dial such that rotation of the first rotatable dial causes rotation of the first rotatable spool; and the second rotatable spool may be attached to a second rotatable dial such that rotation of the second rotatable dial causes rotation of the second rotatable spool. In some embodiments, each of the at least two steering wires is attached to the wall of the tube within the steering channel at the distal end of the tube.

In certain embodiments, the at least two steering wires comprise a first steering wire, a second steering wire, and a third steering wire; and the first steering wire is attached to the wall of the tube within the steering channel at the distal end of the tube, the attachment between the first steering wire and the wall forming a first attachment point; the second steering wire is attached to the wall of the tube within the steering channel at the distal end of the tube, the attachment between the second steering wire and the wall forming a second attachment point; the third steering wire is attached to the wall of the tube within the steering channel at the distal end of the tube, the attachment between the third steering wire and the wall forming a third attachment point; and the third attachment point is closer to the proximal end of the tube than is the first attachment point or the second attachment point.

Some embodiments further comprise a sensing lead positioned at least partially within the first lumen, and some embodiments further comprise a micro-camera system positioned at least partially within the second lumen. Further, a laser Doppler tip may be positioned at least partially within the second lumen.

At least some embodiments disclosed herein include a method of placing a lead in a tissue of a heart, the method comprising: extending into a blood vessel an elongated tube having a proximal end, a distal end, and a first lumen, such that the distal end of the tube is in contact with a targeted tissue on the interior of a wall of the heart; aspirating the targeted tissue such that the wall of the heart is retracted away from a pericardial sac surrounding the heart to enlarge a pericardial space between the pericardial sac and the wall of the heart; accessing the pericardial space through the targeted tissue; inserting at least the distal end of an elongated guide wire into the pericardial space; inserting into the first lumen of the elongated tube and over the elongated guide wire a delivery catheter comprising a first lumen, wherein the first lumen of the delivery catheter has a bend at or near the distal end of the delivery catheter and an outlet at or near the distal end of the delivery catheter; advancing at least the distal end of the delivery catheter through the targeted tissue into the pericardial space; directing the delivery catheter such that the outlet of the first lumen of the delivery catheter is adjacent to the tissue of the heart; extending a lead through the first lumen of the delivery catheter into the tissue of the heart; withdrawing the delivery catheter from the pericardial space; and withdrawing the guide wire from the pericardial space. In some embodiments, the delivery catheter further comprises a steering channel and a steering wire system located at least partially within the steering channel; and the step of directing the delivery catheter such that the outlet of the first lumen of the delivery catheter is adjacent to the tissue of the heart comprises directing the delivery catheter with the steering wire system. Certain embodiments may further comprise the step of extending a laser Doppler tip through a second lumen of the delivery catheter to the pericardial space.

In some embodiments, the lead is a pacing lead; and the steering wire system further comprises at least two steering wires attached to the delivery catheter inside the steering channel and a controller attached to the proximal ends of the at least two steering wires, the controller being capable of collecting and dispensing at least one of the at least two steering wires.

In certain embodiments, the step of directing the delivery catheter using the steering wire system comprises using the controller to tighten at least one of the at least two steering wires.

Certain embodiments may further comprise inserting into the targeted tissue over the guide wire a plug having a first end, a second end, and a hole extending from the first end to the second end. In some embodiments, the hole of the plug is self-sealing after removal of the guide wire.

Other embodiments disclosed herein include a system for closing a hole in cardiac tissue, the system comprising an engagement catheter comprising a proximal end, a distal end, first and second lumens extending between the proximal end and the distal end, and a vacuum port operatively connected to the first lumen of the engagement catheter at the proximal end of the engagement catheter, the vacuum port being capable of operative connection to a vacuum source, wherein the first lumen of the engagement catheter includes a suction port located at or near the distal end of the engagement catheter, the suction port configured to removably attach to a targeted tissue on the interior of a wall of the heart, such that the suction port is capable of forming a reversible seal with the targeted tissue when a vacuum source is operatively attached to the vacuum port; an elongated wire capable of insertion into the second lumen of the engagement catheter; a plug having a first end, a second end, and a hole extending from the first end to the second end, the plug being capable of insertion into the second lumen of the engagement catheter; and an elongated shaft having a proximal end, a distal end, and a lumen extending from the proximal end to the distal end, the elongated shaft being capable of insertion into the second lumen of the engagement catheter; wherein the elongated wire is sized for slidable insertion through the lumen of the shaft and the hole of the plug. The first end of the plug may be radiopaque. In some embodiments, the first end of the plug has a smaller diameter than the second end of the plug. Certain embodiments may include a plug having an external surface that has a screw-shaped ridge.

In some embodiments, the elongated wire comprises a lead, while in other embodiments the elongated wire comprises an elongated guide wire.

At least some disclosed embodiments include a system for closing a hole in cardiac tissue, the system comprising: an engagement catheter comprising a proximal end, a distal end, first and second lumens extending between the proximal end and the distal end, and a vacuum port operatively connected to the first lumen of the engagement catheter at the proximal end of the engagement catheter, the vacuum port being capable of operative connection to a vacuum source, wherein the first lumen of the engagement catheter includes a suction port located at or near the distal end of the engagement catheter, the suction port configured to removably attach to a targeted tissue on the interior of a wall of the heart, such that the suction port is capable of forming a reversible seal with the targeted tissue when a vacuum source is operatively attached to the vacuum port; a delivery catheter comprising a proximal end, a distal end, and a hollow tube extending between the proximal end and the distal end, the delivery catheter configured such that the hollow tube is capable of insertion into the second lumen of the engagement catheter; an elongated delivery wire having a proximal end and a distal end, the distal end of the delivery wire being capable of insertion through the hollow tube of the delivery catheter; and a closure member having a first face and a second face, the closure member being capable of transitioning from a folded configuration within the hollow tube of the delivery catheter to an expanded configuration outside of the hollow tube of the delivery catheter; wherein the first face of the closure member is configured for reversible attachment to the distal end of the delivery wire. In at least some embodiments, the closure member comprises an external cover and an internal cover; the first face of the closure member comprises an outside face of the internal cover; and the second face of the closure member comprises an outside face of the external cover. Further, the internal cover may further comprise an inside face; the external cover may further comprise an inside face; and at least one of the inside face of the internal cover and the inside face of the external cover may comprise a magnet.

In at least some embodiments, the external cover is attached to the internal cover. In some embodiments, the internal cover further comprises an inside face; the external cover further comprises an inside face; and an adhesive is attached to the inside face of the internal cover and the inside face of the external cover.

The closure member may comprise a biodegradable substance. In some embodiments, the closure member comprises nitinol.

Also disclosed herein are embodiments including a method for closing a hole in a targeted tissue of a heart, the method comprising: contacting the targeted tissue in the interior of the heart with a distal end of an elongated tube, the elongated tube having a first lumen and a second lumen; aspirating the targeted tissue such that the targeted tissue is retracted away from a pericardial sac surrounding the heart and a pericardial space between the pericardial sac and the targeted tissue is enlarged; inserting through the first lumen of the elongated tube a delivery catheter having a lumen; inserting an elongated delivery wire through the lumen of the delivery catheter, the elongated delivery wire having an external cover that is capable of transitioning from a folded configuration within the lumen of the delivery catheter to an expanded configuration outside of the lumen of the delivery catheter, the external cover being reversibly attached to a distal end of the delivery wire; delivering the external cover through the hole in the targeted tissue into the pericardial space; placing the external cover onto the targeted tissue from the pericardial space; releasing the external cover from the delivery wire; and withdrawing the delivery wire from the targeted tissue. In some embodiments, the method further comprises the steps of: reversibly attaching an internal cover to the distal end of the delivery wire, the internal cover being capable of transitioning from a folded configuration within the lumen of the delivery catheter to an expanded configuration outside of the lumen of the delivery catheter; delivering the internal cover to the targeted tissue in the interior of the heart; placing the internal cover onto the targeted tissue from the interior of the heart; releasing the internal cover from the delivery wire; and withdrawing the delivery wire from the interior of the heart.

At least some embodiments include a method for closing a hole in a targeted tissue of a heart, the method comprising: providing access to the hole in the targeted tissue by inserting a wire through a lumen of an elongated tube and through the hole in the targeted tissue, the elongated tube having a proximal end and a distal end adjacent to the targeted tissue; inserting into the lumen of the elongated tube and over the wire a plug having a first end, a second end, and a hole extending from the first end to the second end; inserting into the lumen of the elongated tube and over the wire an elongated shaft having a proximal end, a distal end, and a hole extending from the proximal end to the distal end; sliding the elongated shaft toward the distal end of the elongated tube until the plug approaches the hole in the targeted tissue; inserting the plug into the hole in the targeted tissue; and withdrawing the elongated shaft from the elongated tube. In some embodiments, the first end of the plug has a diameter that is smaller than the diameter of the second end of the plug, and the first end of the plug may be radiopaque. The embodiment may further comprise the step of confirming the location of the plug using radiographic imaging.

In at least some embodiments, the wire comprises a guide wire, and the hole of the plug closes after the guide wire is withdrawn from the hole of the plug.

Certain embodiments include a delivery catheter for use in accessing a pericardial space surrounding the external surface of a heart, comprising: an elongated tube comprising a wall extending from a proximal end of the tube to a distal end of the tube, a first lumen, and a second lumen; wherein the first lumen extends from approximately the proximal end of the tube to or near the distal end of the tube, the first lumen having a bend, relative to the tube, at or near the distal end of the tube and an outlet through the wall of the tube at or near the distal end of the tube; and wherein the second lumen extends from approximately the proximal end of the tube to or near the distal end of the tube, the second lumen having a bend, relative to the tube, at or near the distal end of the tube and an outlet through the wall of the tube at or near the distal end of the tube. The bend of the first lumen may form an angle that is approximately 90-degrees, and the bend of the second lumen may form an angle that is approximately 90-degrees.

At least some embodiments further comprise a laser Doppler tip positioned at least partially within the second lumen. A needle may be positioned at least partially within the first lumen.

Disclosed herein are embodiments including a method of injecting a substance into a cardiac tissue from the pericardial space surrounding the external surface of a heart, the method comprising: extending into a blood vessel an elongated tube having a proximal end, a distal end, and a first lumen, such that the distal end of the tube is in contact with a targeted tissue on the interior of a wall of the heart; aspirating the targeted tissue such that the wall of the heart is retracted away from a pericardial sac surrounding the heart to enlarge a pericardial space between the pericardial sac and the wall of the heart; accessing the pericardial space through the targeted tissue; inserting at least the distal end of an elongated guide wire into the pericardial space; inserting into the first lumen of the elongated tube and over the elongated guide wire a delivery catheter comprising a first lumen, wherein the first lumen of the delivery catheter has a bend at or near the distal end of the delivery catheter and an outlet at or near the distal end of the delivery catheter; advancing at least the distal end of the delivery catheter through the targeted tissue into the pericardial space; directing the delivery catheter such that the outlet of the first lumen of the delivery catheter is adjacent to the external surface of the heart; extending a needle through the first lumen of the delivery catheter into the cardiac tissue; injecting the substance into the cardiac tissue; and withdrawing the delivery catheter from the pericardial space. The substance may comprise gene cells, growth factors, and/or a biodegradable synthetic polymer. The biodegradable synthetic polymer may be selected from the group consisting of polylactides, polyglycolides, polycaprolactones, polyanhydrides, polyamides, and polyurethanes. In certain embodiments, the substance comprises a tissue inhibitor, such as a metalloproteinase. In at least certain embodiments, the substance comprises RGD-liposome biologic glue.

In at least some embodiments, the delivery catheter further comprises a second lumen, wherein the second lumen of the delivery catheter has a bend at or near the distal end of the delivery catheter and an outlet at or near the distal end of the delivery catheter. The delivery catheter may further comprise a laser Doppler tip. In some embodiments, the method further comprises the step of measuring the thickness of the cardiac tissue using the laser Doppler tip.

Certain embodiments include a system for closing a hole in a targeted tissue, comprising: a closure member having a head and a plurality of arms extending from the head, the closure member capable of transitioning between an open position and a closed position; and a delivery catheter comprising a proximal end, a distal end, and a hollow tube extending between the proximal end and the distal end, the delivery catheter configured such that the closure member is capable of insertion into the hollow tube when the closure member is in the open position. In at least some embodiments, the system further comprises an engagement catheter comprising a proximal end, a distal end, a first lumen extending between the proximal end and the distal end, and a vacuum port operatively connected to the first lumen of the engagement catheter at the proximal end of the engagement catheter, the vacuum port being capable of operative connection to a vacuum source, wherein the first lumen of the engagement catheter includes a suction port located at or near the distal end of the engagement catheter, the suction port configured to removably attach to a targeted tissue on the interior of a wall of the heart, such that the suction port is capable of forming a reversible seal with the targeted tissue when a vacuum source is operatively attached to the vacuum port; wherein the delivery catheter is configured for inserted into the first lumen of the engagement catheter.

The plurality of arms of the closure member may comprise nitinol. In some embodiments, the plurality of arms of the closure member comprise four arms.

In at least certain embodiments, a method for closing a hole in a targeted tissue of a heart, the method comprises: providing a closure member having a head and a plurality of arms extending from the head, the closure member capable of transitioning between an open position and a closed position; delivering the closure member to the heart through a delivery catheter comprising a proximal end, a distal end, and a hollow tube extending between the proximal end and the distal end, the delivery catheter configured such that the closure member is capable of insertion into the hollow tube when the closure member is in the open position; deploying the closure member such that the closure member contacts the targeted tissue and transitions to the closed position. The step of delivery the closure member to the heart may comprise advancing the closure member through the delivery catheter by pushing on the head of the closure member using a rod inserted into the hollow tube.

BRIEF DESCRIPTION OF THE DRAWINGS

FIG. 1A shows an embodiment of an engagement catheter and an embodiment of a delivery catheter as disclosed herein;

FIG. 1B shows a percutaneous intravascular pericardial delivery using another embodiment of an engagement catheter and another embodiment of a delivery catheter as disclosed herein;

FIG. 2A shows a percutaneous intravascular technique for accessing the pericardial space through a right atrial wall or atrial appendage using the engagement and delivery catheters shown in FIG. 1A;

FIG. 2B shows the embodiment of an engagement catheter shown in FIG. 2A;

FIG. 2C shows another view of the distal end of the engagement catheter embodiment shown in FIGS. 2A and 2B;

FIG. 4A to 4C show a closure of a hole in the atrial wall using an embodiment as disclosed herein;

FIG. 4F shows still another closure of a hole in cardiac tissue using another embodiment as disclosed herein;

FIG. 5A shows an embodiment of an engagement catheter as disclosed herein;

FIG. 5B shows a cross-sectional view of the proximal end of the engagement catheter shown in FIG. 5A;

FIG. 5C shows a cross-sectional view of the distal end of the engagement catheter shown in FIG. 5A;

FIG. 6A shows an embodiment of a delivery catheter as disclosed herein;

FIG. 6B shows a close-up view of the needle shown in FIG. 6A;

FIG. 6C shows a cross-sectional view of the needle shown in FIGS. 6A and 6B;

FIG. 11 shows a cross-sectional view of another embodiment of a delivery catheter as disclosed herein;

FIG. 14 shows another embodiment of a system for closing a hole in cardiac tissue, as disclosed herein;

FIG. 15A shows another embodiment of a system for closing a hole in cardiac tissue, as disclosed herein;

FIG. 15B shows the embodiment of FIG. 15A approaching cardiac tissue; and

FIG. 15C shows the embodiment of FIGS. 15A-15C deployed on the cardiac tissue.

DETAILED DESCRIPTION

Figures 3A, 3B:
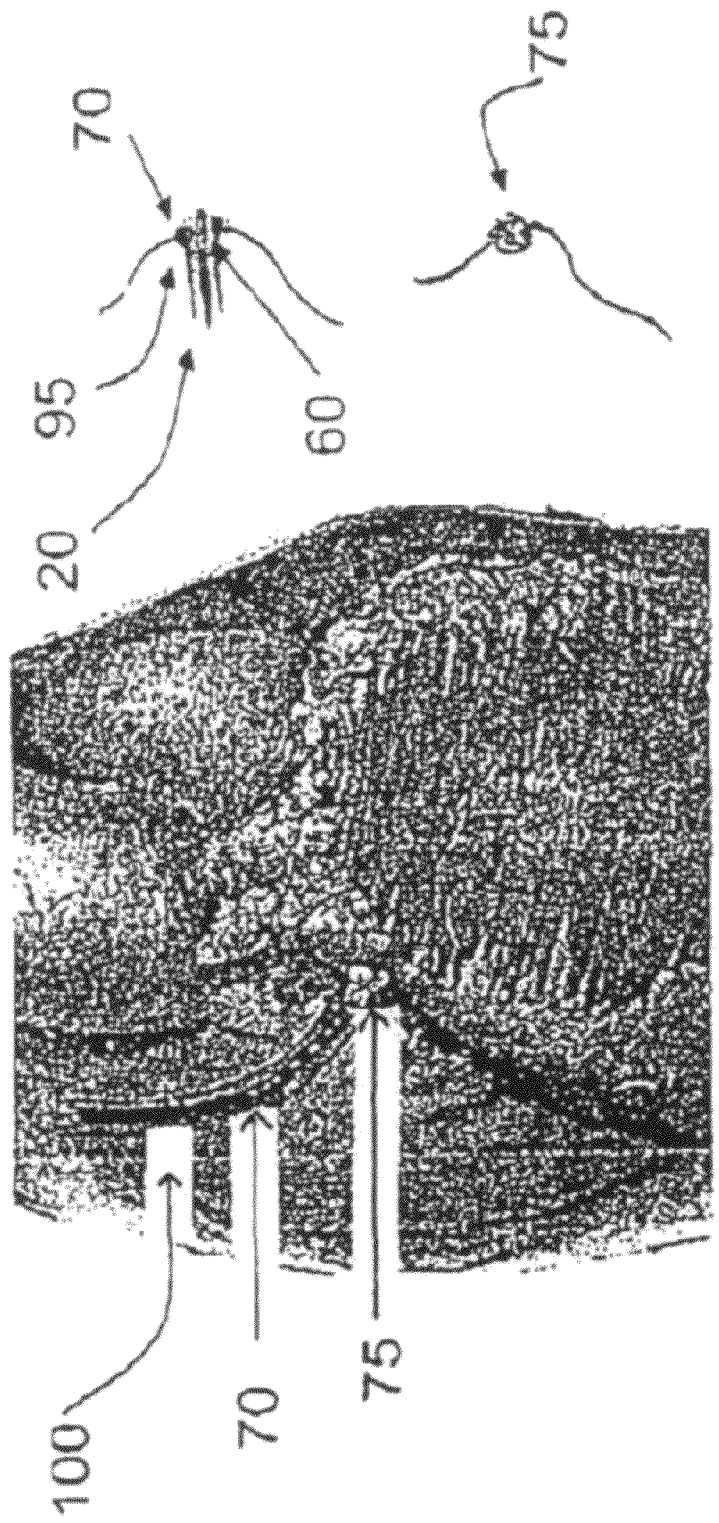
FIG. 3A shows removal of an embodiment of a catheter as disclosed herein.
FIG. 3B shows the resealing of a puncture according to an embodiment as disclosed herein.

It will be appreciated by those of skill in the art that the following detailed description of the disclosed embodiments is merely exemplary in nature and is not intended to limit the scope of the appended claims.

The disclosed embodiments include devices, systems, and methods useful for accessing various tissues of the heart from inside the heart. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, as explained in more detail below, epicardial pacing leads may be delivered via the pericardial space, and an ablation catheter may be used on the epicardial tissue from the pericardial space.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter.

As shown in more detail in FIGS. 2A, 2B, 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Flouroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transseptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Referring now to FIG. 3A, the catheter system shown in FIG. 1B is retrieved by pull back through the route of entry. However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity or the heart, as discussed herein; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Figure 4D:
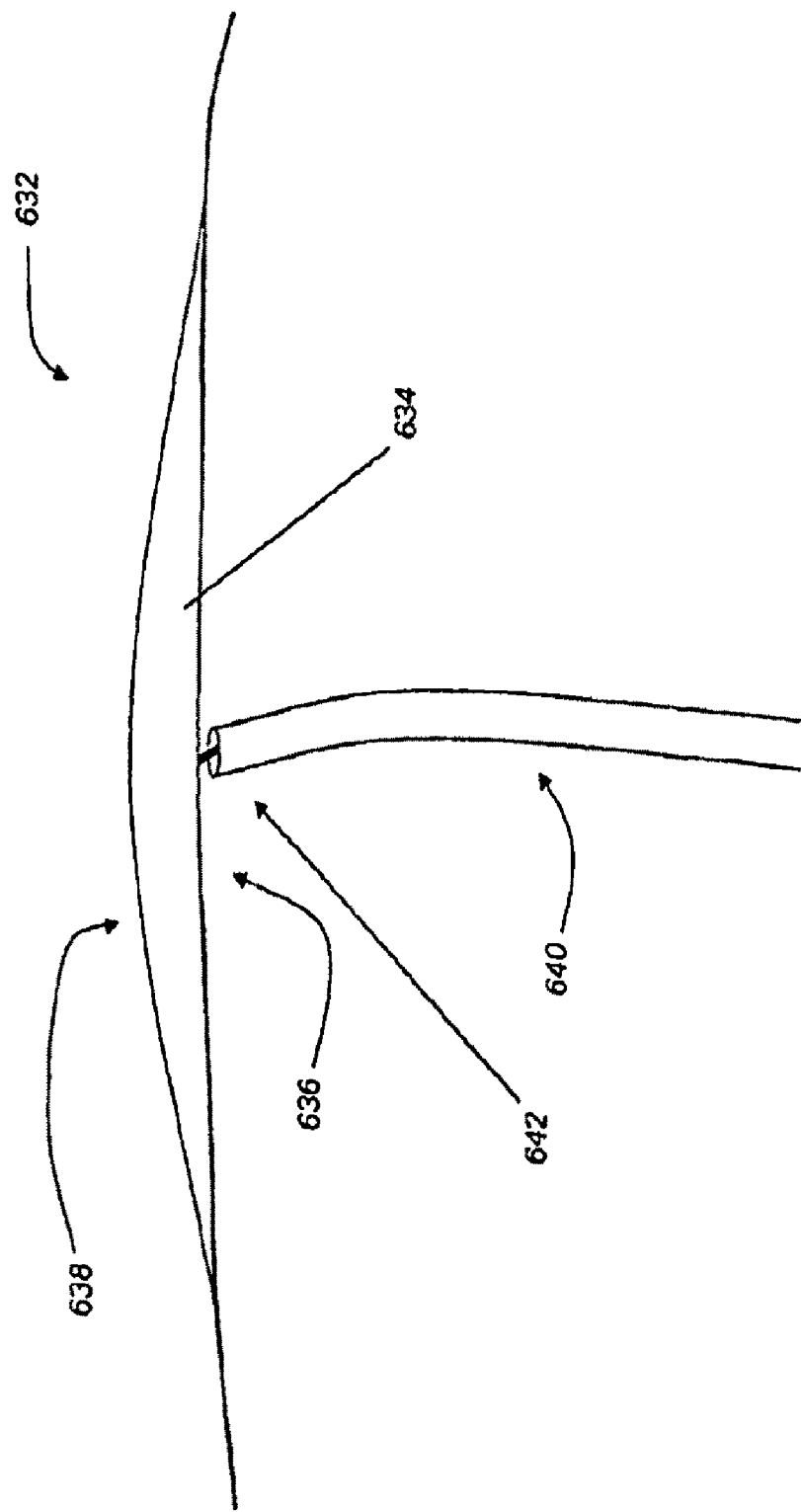
FIG. 4D shows another closure of a hole in cardiac tissue using another embodiment as disclosed herein.

Other examples for sealing the puncture wound in the atrial wall or appendage are shown in FIGS. 4A-4F. Referring now to FIGS. 4A-4C, a sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded to an expanded configuration once it is outside of the catheter. As shown in FIG. 4A, external cover 610 is deployed (in its expanded configuration) on the outside of the atrial wall to seal a puncture wound in the targeted tissue, having already been delivered through the puncture wound into the pericardial space. Internal cover 620 is delivered through engagement catheter 600 (in its folded configuration), as shown in FIGS. 4A and 4B, by an elongated delivery wire 615, to which internal cover 620 is reversibly attached (for example, by a screw-like mechanism). Once internal cover 620 is in position on the inside of atrial wall 630 at the targeted tissue, internal cover 620 is deployed to help seal the puncture wound in the targeted tissue (see FIG. 4C).

Internal cover 620 and external cover 610 may be made from a number of materials, including a shape-memory alloy such as nitinol. Such embodiments are capable of existing in a catheter in a folded configuration and then expanding to an expanded configuration when deployed into the body. Such a change in configuration can result from a change in temperature, for example. Other embodiments of internal and external covers may be made from other biocompatible materials and deployed mechanically.

After internal cover 620 is deployed, engagement catheter 600 releases its grip on the targeted tissue and is withdrawn, leaving the sandwich-type closure to seal the puncture wound, as shown in FIG. 4C. External cover 610 and internal cover 620 may be held in place using a biocompatible adhesive. Similarly, external cover 610 and internal cover 620 may be held in place using magnetic forces, such as, for example, by the inside face (not shown) of external cover 610 comprising a magnet, by the inside face (not shown) of internal cover 620 comprising a magnet, or both inside faces of external cover 610 or internal cover 620 comprising magnets.

In the embodiment shown in FIGS. 4A, 4B, and 4C, the closure member comprises external cover 610 and internal cover 620. However, in at least certain other embodiments, the closure member need not have two covers. For example, as shown in FIG. 4D, closure member 632 is made of only one cover 634. Cover 634 has a first face 636 and a second face 638, and first face 636 is configured for reversible attachment to distal end 642 of delivery wire 640. Closure member 632 may be made of any suitable material, including nitinol, which is capable of transitioning from a folded configuration to an expanded configuration.

Figure 4E:
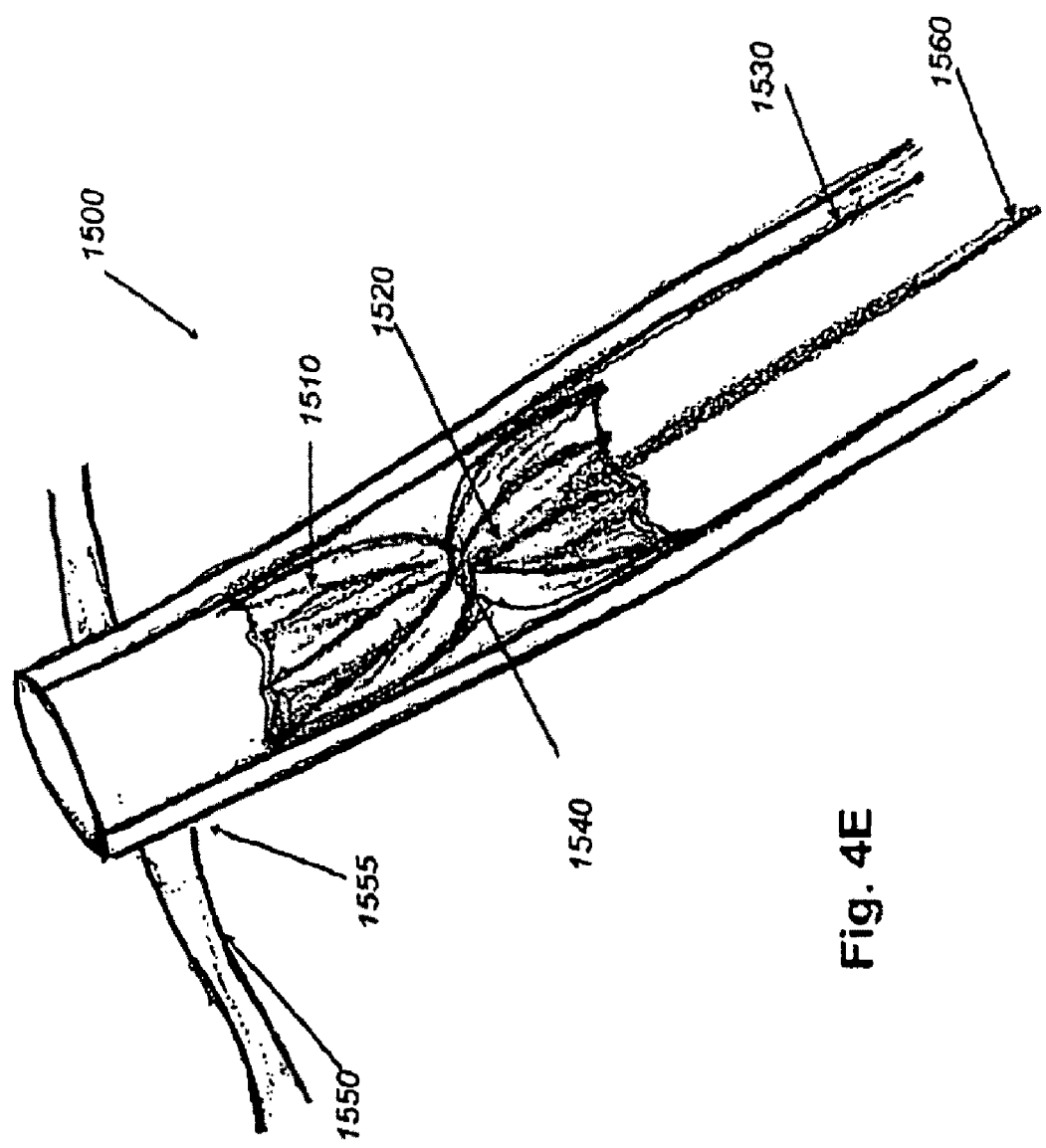
FIG. 4E shows yet another closure of a hole in cardiac tissue using another embodiment as disclosed herein.

In the embodiment shown in FIG. 4E, a closure member 1500 comprises an external cover 1510 and an internal cover 1520 within a delivery catheter 1530. External cover 1510 and internal cover 1520 are attached at a joint 1540, which may be formed, for example, by a mechanical attachment or by a magnetic attachment. In embodiments having a magnetic attachment, each of the external cover and the internal cover may have a ferromagnetic component that is capable of magnetically engaging the other ferromagnetic component.

Delivery catheter 1530 is shown after insertion through hole 1555 of atrial wall 1550. Closure member 1500 may be advanced through delivery catheter 1530 to approach atrial wall 1550 by pushing rod 1560. Rod 1560 may be reversibly attached to internal cover 1520 so that rod 1560 may be disconnected from internal cover 1520 after closure member 1500 is properly deployed. For example, rod 1560 may engage internal cover 1520 with a screw-like tip such that rod 1560 may be easily unscrewed from closure member 1500 after deployment is complete. Alternatively, rod 1560 may simply engage internal cover 1520 such that internal cover 1520 may be pushed along the inside of delivery catheter 1530 without attachment between internal cover 1520 and rod 1560.

Closure member 1500 is advanced through delivery catheter 1530 until external cover 1510 reaches a portion of delivery catheter 1530 adjacent to atrial wall 1550; external cover 1510 is then pushed slowly out of delivery catheter 1530 into the pericardial space. External cover 1510 then expands and is positioned on the outer surface of atrial wall 1550. When external cover 1510 is properly positioned on atrial wall 1550, joint 1540 is approximately even with atrial wall 1550 within hole 1555. Delivery catheter 1530 is then withdrawn slowly, causing hole 1555 to close slightly around joint 1540. As delivery catheter 1530 continues to be withdrawn, internal cover 1520 deploys from delivery catheter 1530, thereby opening into its expanded formation. Consequently, atrial wall 1550 is pinched between internal cover 1520 and external cover 1510, and hole 1555 is closed to prevent leakage of blood from the heart.

FIG. 4F shows the occlusion of a hole (not shown) in atrial wall 1600 due to the sandwiching of atrial wall 1600 between an external cover 1610 and an internal cover 1620. External cover 1610 is shown deployed on the outside surface of atrial wall 1600, while internal cover 1620 is deployed on the inside surface of atrial wall 1600. As shown, rod 1640 is engaged with internal cover 1620, and delivery catheter 1630 is in the process of being withdrawn, which allows internal cover 1620 to fully deploy. Rod 1640 is then withdrawn through delivery catheter 1630. An engagement catheter (not shown) may surround delivery catheter 1650, as explained more fully herein.

Other examples for sealing a puncture wound in the cardiac tissue are shown in FIGS. 12-15. Referring now to FIG. 12A, there is shown a plug 650 having a first end 652, a second end 654, and a hole 656 extending from first end 652 to second end 654. Plug 650 may be made from any suitable material, including casein, polyurethane, silicone, and polytetrafluoroethylene. Wire 660 has been slidably inserted into hole 656 of plug 650. Wire 660 may be, for example, a guide wire or a pacing lead, so long as it extends through the hole in the cardiac tissue (not shown). As shown in FIG. 12A, first end 652 is covered with a radiopaque material, such as barium sulfate, and is therefore radiopaque. This enables the clinician to view the placement of the plug in the body using radiographic imaging. For example, the clinician can confirm the location of the plug during the procedure, enabling a safer and more effective procedure for the patient.

Figure 12C:
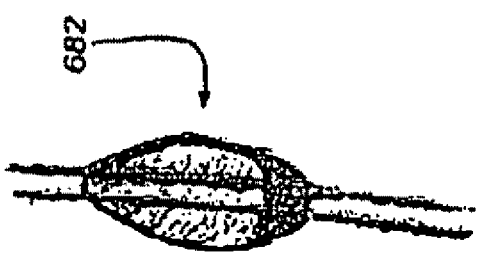
FIG. 12C shows another embodiment of a system for closing a hole in cardiac tissue, as disclosed herein.
Figure 12B:
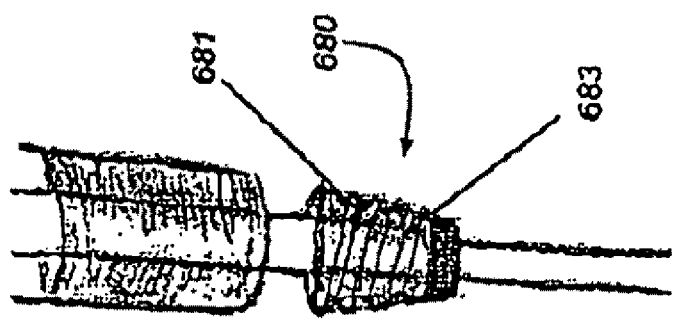
FIG. 12B shows another embodiment of a system for closing a hole in cardiac tissue, as disclosed herein.
Figure 12A:
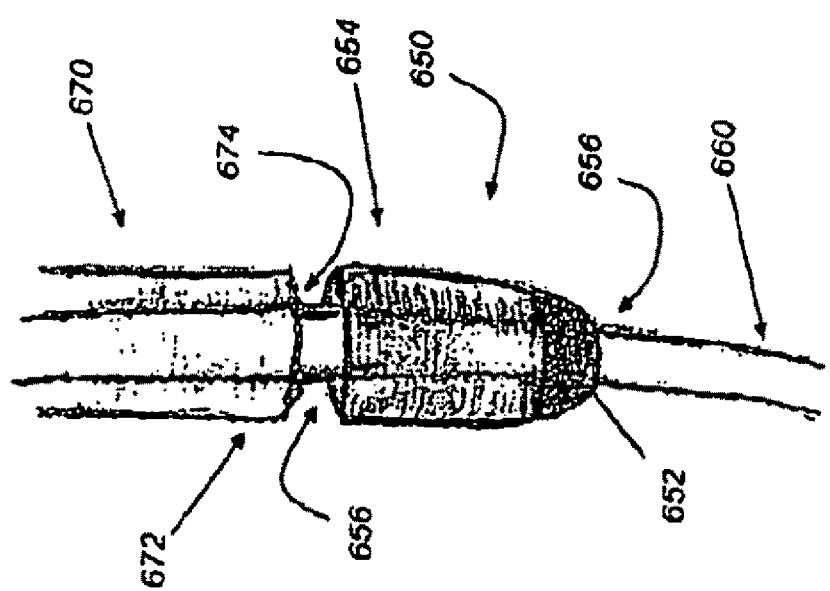
FIG. 12A shows an embodiment of a system for closing a hole in cardiac tissue, as disclosed herein.

As shown in FIG. 12A, first end 652 of plug 650 has a smaller diameter than second end 654 of plug 650. Indeed, plug 680 shown FIG. 12B and plug 684 shown in FIGS. 13 and 14 have first ends that are smaller in diameter than their respective second ends. However, not all embodiments of plug have a first end that is smaller in diameter than the second end. For example, plug 682 shown in FIG. 12C has a first end with a diameter that is not smaller than the diameter of the second end. Both types of plug can be used to close holes in cardiac tissue.

Referring again to FIG. 12A, elongated shaft 670 has a proximal end (not shown), a distal end 672, and a lumen 674 extending from the proximal end to distal end 672. Although no catheter is shown in FIG. 12A, plug 650, wire 660, and shaft 670 are configured for insertion into a lumen of a catheter (see FIG. 14), such as an embodiment of an engagement catheter disclosed herein. Plug 650 and shaft 670 are also configured to be inserted over wire 660 and can slide along wire 660 because each of lumen 656 of plug 650 and lumen 674 of shaft 670 is slightly larger in circumference than wire 660.

Figure 13:
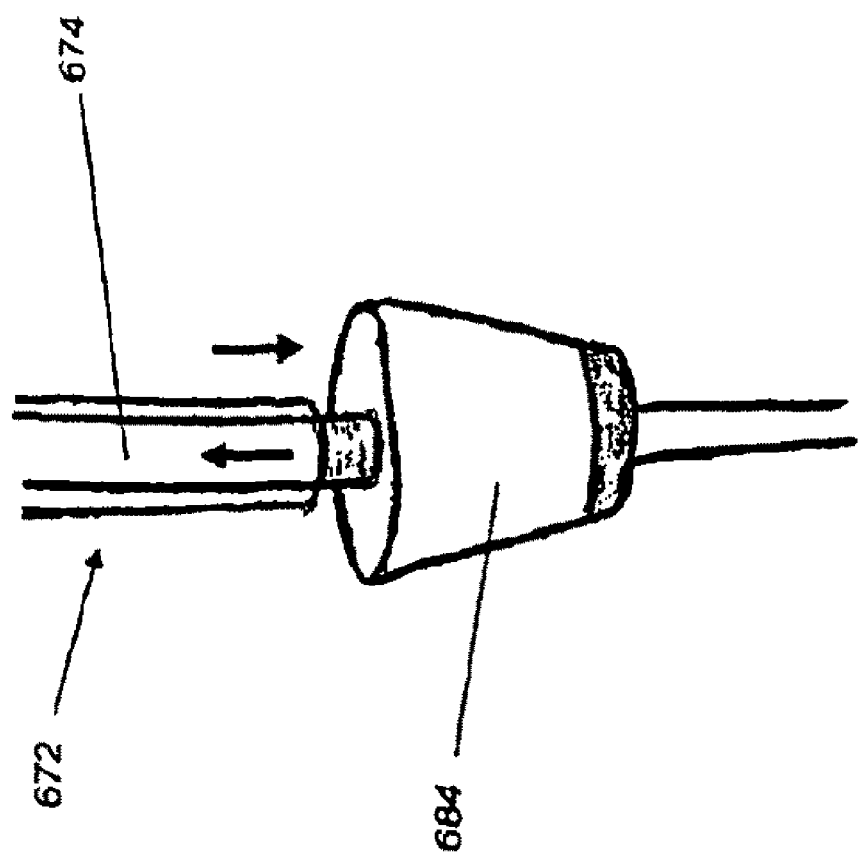
FIG. 13 shows another embodiment of a system for closing a hole in cardiac tissue, as disclosed herein.

As shown in FIGS. 13 and 14, shaft 672 is used to push plug 684 along wire 674 within elongated tube 676 to and into the hole in the targeted cardiac tissue 678. Distal end 677 of elongated tube 676 is shown attached to cardiac tissue 678, but distal end 677 need not be attached to cardiac tissue 678 so long as distal end 677 is adjacent to cardiac tissue 678. Once plug 684 is inserted into the hole, wire 674 may be withdrawn from the hole in plug 684 and the interior of the heart (not shown) and shaft 672 is withdrawn from elongated tube 676. In some embodiments, the plug is self-sealing, meaning that the hole of the plug closes after the wire is withdrawn. For example, the plug may be made from a dehydrated protein matrix, such as casein or ameroid, which swells after soaking up fluid. After shaft 672 is withdrawn, elongated tube 676 can be withdrawn from the heart.

It should be noted that, in some embodiments, the wire is not withdrawn from the hole of the plug. For example, where the wire is a pacing lead, the wire may be left within the plug so that it operatively connects to the CRT device.

Referring now to FIG. 12B, there is shown a plug 680 that is similar to plug 684. However, plug 680 comprises external surface 681 having a ridge 683 that surrounds plug 680 in a helical or screw-like shape. Ridge 683 helps to anchor plug 680 into the hole of the targeted tissue (not shown). Other embodiments of plug may include an external surface having a multiplicity of ridges surrounding the plug, for example, in a circular fashion.

FIGS. 15A-15C show yet another embodiment of a closure member for closing a hole in a tissue. Spider clip 1700 is shown within catheter 1702 and comprises a head 1705 and a plurality of arms 1710, 1720, 1730, and 1740. Each of arms 1710, 1720, 1730, and 1740 is attached at its proximal end to head 1705. Although spider clip 1700 has four arms, other embodiments of spider clip include fewer than, or more than, four arms. For example, some embodiments of spider clip have three arms, while others have five or more arms.

Referring again to FIGS. 15A-15C, arms 1710, 1720, 1730, and 1740 may be made from any flexible biocompatible metal that can transition between two shapes, such as a shape-memory alloy (e.g., nitinol) or stainless steel. Spider clip 1700 is capable of transitioning between an open position (see FIG. 15A), in which the distal ends of its arms 1710, 1720, 1730, and 1740 are spaced apart, and a closed position (see FIG. 15C), in which the distal ends of arms 1710, 1720, 1730, and 1740 are gathered together. For embodiments made from a shape-memory alloy, the clip can be configured to transition from the open position to the closed position when the metal is warmed to approximately body temperature, such as when the clip is placed into the cardiac tissue. For embodiments made from other types of metal, such as stainless steel, the clip is configured in its closed position, but may be transitioned into an open position when pressure is exerted on the head of the clip. Such pressure causes the arms to bulge outward, thereby causing the distal ends of the arms to separate.

In this way, spider clip 1700 may be used to seal a wound or hole in a tissue, such as a hole through the atrial wall. For example, FIG. 15B shows spider clip 1700 engaged by rod 1750 within engagement catheter 1760. As shown, engagement catheter 1760 has a bell-shaped suction port 1765, which, as disclosed herein, has aspirated cardiac tissue 1770. Cardiac tissue 1770 includes a hole 1775 therethrough, and suction port 1765 fits over hole 1775 so as to expose hole 1775 to spider clip 1700.

Rod 1750 pushes spider clip 1700 through engagement catheter 1760 to advance spider clip 1700 toward cardiac tissue 1770. Rod 1750 simply engages head 1705 by pushing against it, but in other embodiments, the rod may be reversibly attached to the head using a screw-type system. In such embodiments, the rod may be attached and detached from the head simply by screwing the rod into, or unscrewing the rod out of, the head, respectively.

In at least some embodiments, the spider clip is held in its open position during advancement through the engagement catheter by the pressure exerted on the head of the clip by the rod. This pressure may be opposed by the biasing of the legs against the engagement catheter during advancement.

Referring to FIG. 15C, spider clip 1700 approaches cardiac tissue 1770 and eventually engages cardiac tissue 1770 such that the distal end of each of arms 1710, 1720, 1730, and 1740 contacts cardiac tissue 1770. Rod 1750 is disengaged from spider clip 1700, and spider clip 1700 transitions to its closed position, thereby drawing the distal ends of arms 1710, 1720, 1730, and 1740 together. As the distal ends of the arms are drawn together, the distal ends grip portions of cardiac tissue 1770, thereby collapsing the tissue between arms 1710, 1720, 1730, and 1740 such that hole 1775 is effectively closed.

Rod 1750 is then withdrawn, and engagement catheter 1760 is disengaged from cardiac tissue 1770. The constriction of cardiac tissue 1770 holds hole 1775 closed so that blood does not leak through hole 1775 after engagement catheter 1760 is removed. After a relatively short time, the body's natural healing processes permanently close hole 1775. Spider clip 1700 may remain in the body indefinitely.

Referring now to FIGS. 5A, 5B, 5C, and 5D, there is shown another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

Figure 5D:
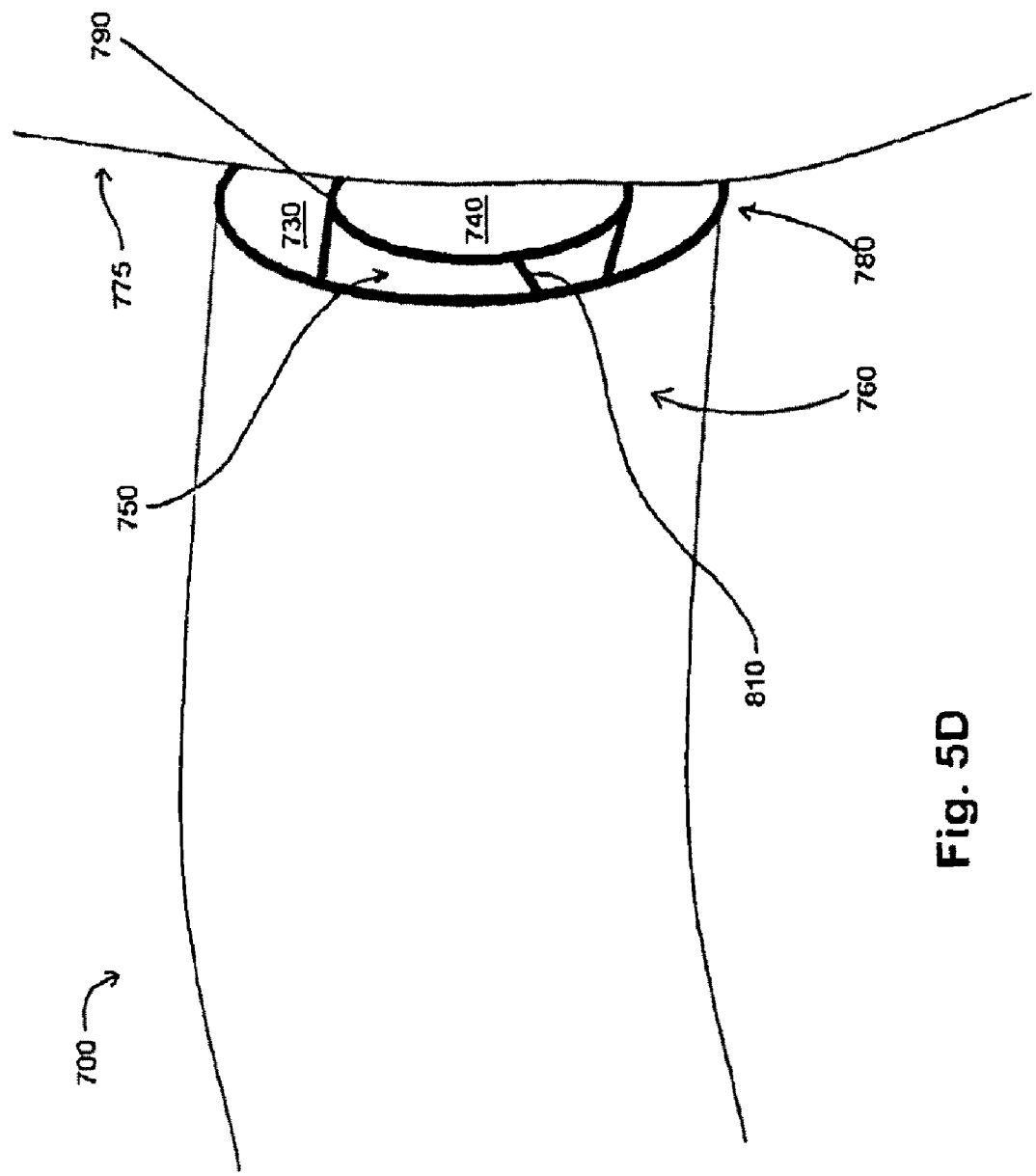
FIG. 5D shows the engagement catheter shown in FIG. 5A approaching a heart wall from inside of the heart.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tampondae) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads (as discussed herein); (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 7:
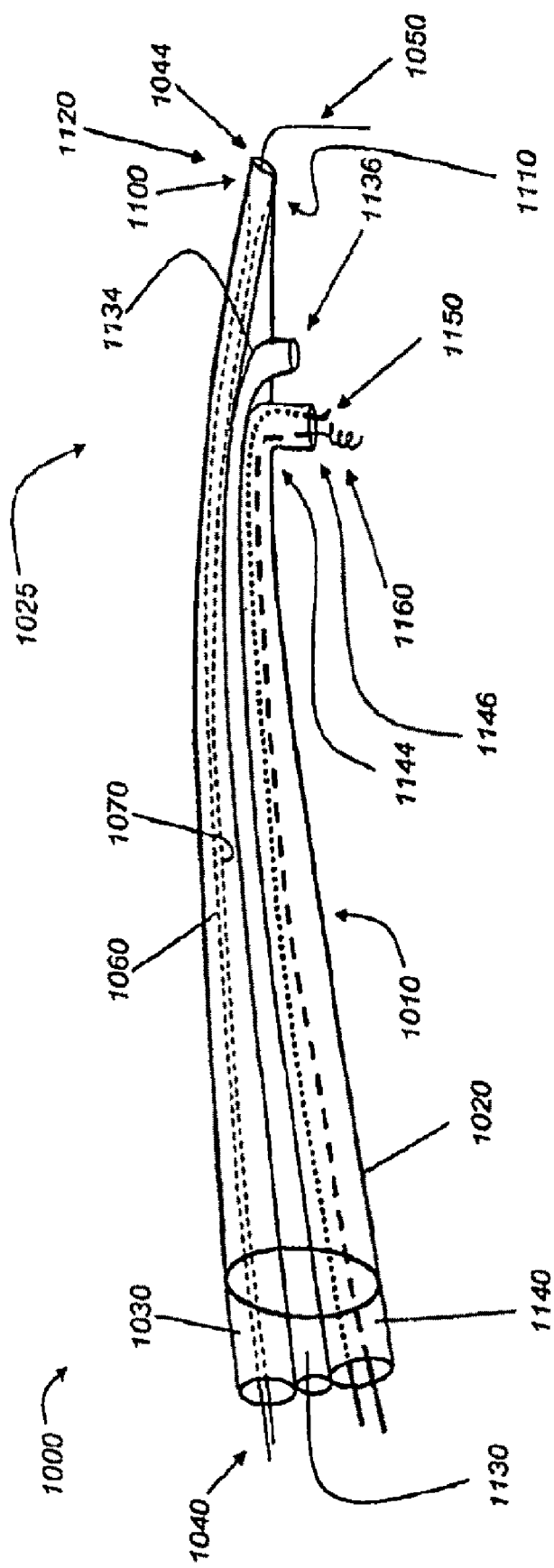
FIG. 7 shows an embodiment of a delivery catheter as disclosed herein.

Referring now to FIG. 7, there is shown a delivery catheter 1000. Delivery catheter 1000 includes an elongated tube 1010 having a wall 1020 extending from a proximal end (not shown) of tube 1010 to a distal end 1025 of tube 1010. Tube 1010 includes two lumens, but other embodiments of delivery catheters may have fewer than, or more than, two lumens, depending on the intended use of the delivery catheter. Tube 1010 also includes a steering channel 1030, in which a portion of steering wire system 1040 is located. Steering channel 1030 forms orifice 1044 at distal end 1025 of tube 1010 and is sized to fit over a guide wire 1050.

Figure 8:
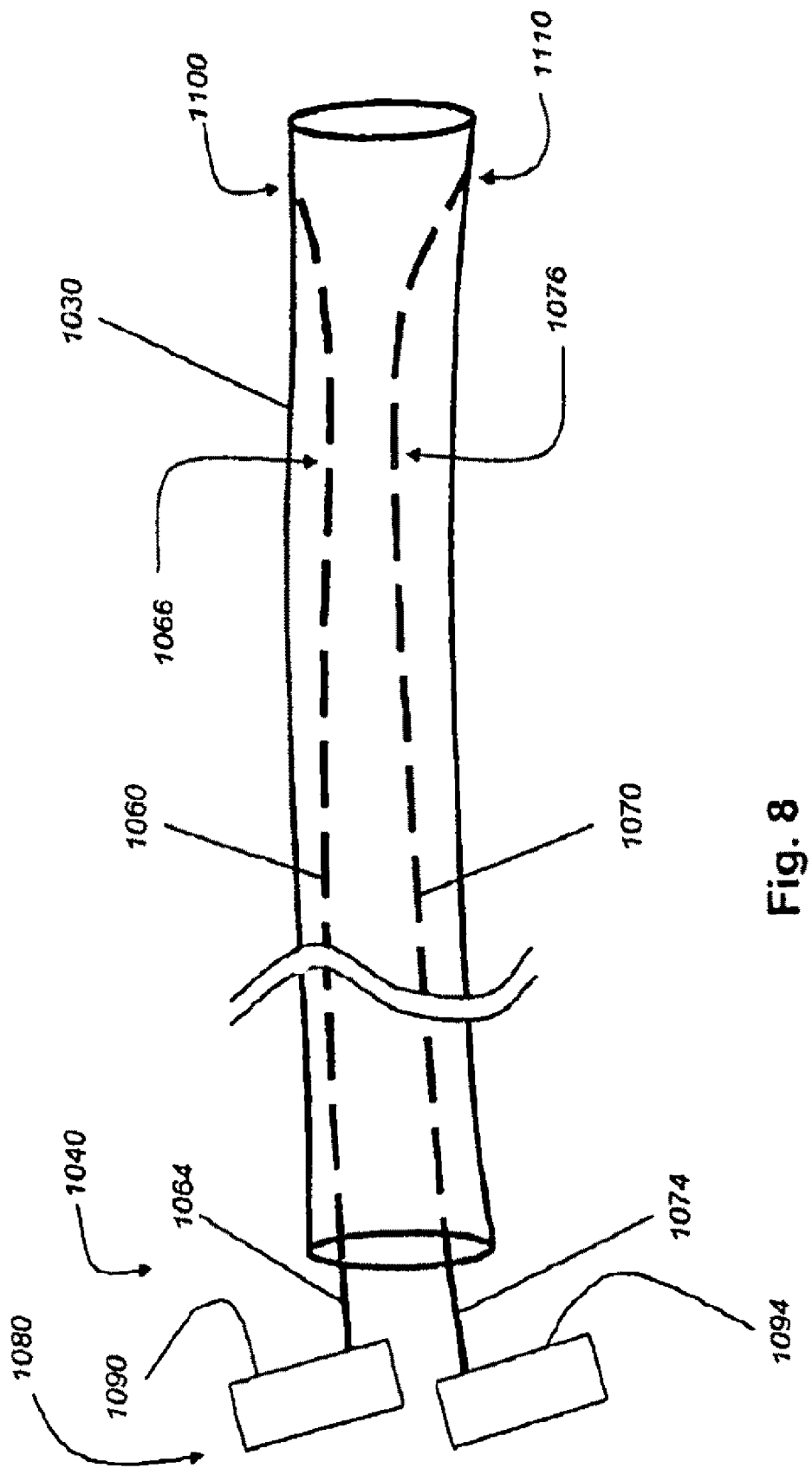
FIG. 8 shows an embodiment of a steering wire system within a steering channel.

FIG. 8 shows in more detail steering wire system 1040 within steering channel 1030 (which is shown cut away from the remainder of the delivery catheter). Steering wire system 1040 is partially located in steering channel 1030 and comprises two steering wires 1060 and 1070 and a controller 1080, which, in the embodiment shown in FIG. 8, comprises a first handle 1090 and a second handle 1094. First handle 1090 is attached to proximal end 1064 of steering wire 1060, and second handle 1094 is attached to proximal end 1074 of steering wire 1070. Distal end 1066 of steering wire 1060 is attached to the wall of the tube of the delivery catheter within steering channel 1030 at attachment 1100, and distal end 1076 of steering wire 1070 is attached to the wall of the tube of the delivery catheter within steering channel 1030 at attachment 1110. As shown in FIG. 7, attachment 1100 and attachment 1110 are located on opposing sides of steering channel 1030 near distal tip 1120 of delivery catheter 1000.

In the embodiment of FIG. 8, steering wires 1060 and 1070 are threaded as a group through steering channel 1030. However, the steering wire systems of other embodiments may include steering wires that are individually threaded through smaller lumens within the steering channel. For example, FIG. 11 shows a cross-sectional view of a delivery catheter 1260 having an elongated tube 1264 comprising a wall 1266, a steering channel 1290, a first lumen 1270, and a second lumen 1280. Delivery catheter 1260 further includes a steering wire 1292 within a steering wire lumen 1293, a steering wire 1294 within a steering wire lumen 1295, and a steering wire 1296 within a steering wire lumen 1297. Each of steering wire lumens 1293, 1295, and 1297 is located within steering channel 1290 and is formed from wall 1266. Each of steering wires 1292, 1294, and 1296 is attached to wall 1266 within steering channel 1290. As will be explained, the attachment of each steering wire to the wall may be located near the distal tip of the delivery catheter, or may be located closer to the middle of the delivery catheter.

Referring now to FIGS. 7 and 8, steering wire system 1040 can be used to control distal tip 1120 of delivery catheter 1000. For example, when first handle 1090 is pulled, steering wire 1060 pulls distal tip 1120, which bends delivery catheter 1000, causing tip deflection in a first direction. Similarly, when second handle 1094 is pulled, steering wire 1070 pulls distal tip 1120 in the opposite direction, which bends delivery catheter 1000, causing tip deflection in the opposite direction. Thus, delivery catheter 1000 can be directed (i.e., steered) through the body using steering wire system 1040.

Although steering wire system 1040 has only two steering wires, other embodiments of steering wire systems may have more than two steering wires. For example, some embodiments of steering wire systems may have three steering wires (see FIG. 11), each of which is attached to the steering channel at a different attachment. Other embodiments of steering wire systems may have four steering wires. Generally, more steering wires give the clinician more control for directing the delivery catheter because each additional steering wire enables the user to deflect the tip of the delivery catheter in an additional direction. For example, four steering wires could be used to direct the delivery catheter in four different directions (e.g., up, down, right, and left).

Figure 9:
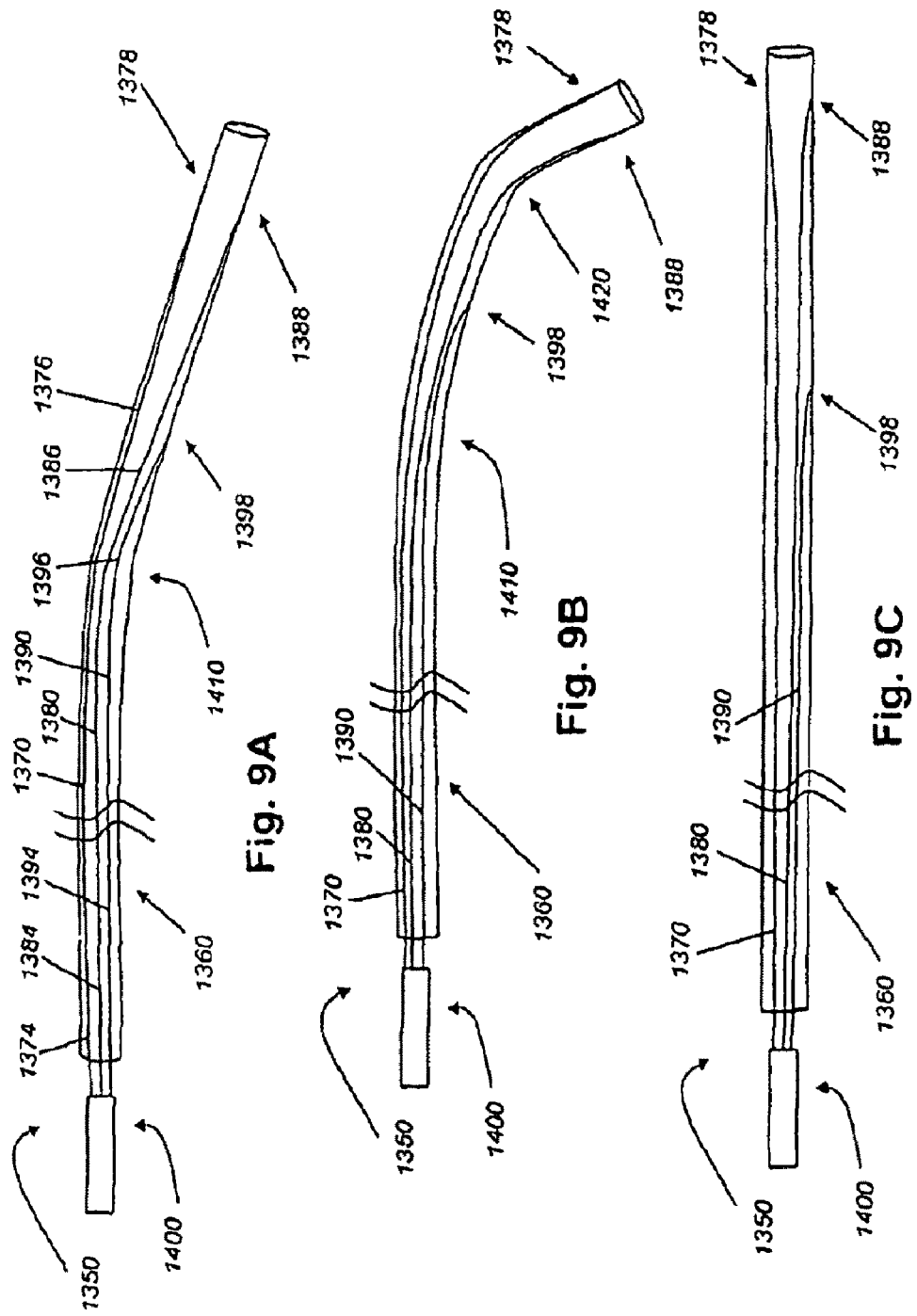
FIG. 9A shows another embodiment of a steering wire system as disclosed herein, the embodiment being deflected in one location.
FIG. 9B shows the steering wire system shown in FIG. 9A, wherein the steering wire system is deflected at two locations.
FIG. 9C shows the steering wire system shown in FIGS. 9A and 9B in its original position.

If a steering wire system includes more than two steering wires, the delivery catheter may be deflected at different points in the same direction. For instance, a delivery catheter with three steering wires may include two steering wires for deflection in a certain direction and a third steering wire for reverse deflection (i.e., deflection in the opposite direction). In such an embodiment, the two steering wires for deflection are attached at different locations along the length of the delivery catheter. Referring now to FIGS. 9A-9C, there is shown a steering wire system 1350 within steering channel 1360 (which is shown cut away from the remainder of the delivery catheter) in different states of deflection. Steering wire system 1350 is partially located in steering channel 1360 and comprises three steering wires 1370, 1380, and 1390 and a controller 1400, which, in the embodiment shown in FIGS. 9A-9C, comprises a handle 1405. Handle 1405 is attached to proximal end 1374 of steering wire 1370, proximal end 1384 of steering wire 1380, and proximal end 1394 of steering wire 1390. Distal end 1376 of steering wire 1370 is attached to the wall of the tube of the delivery catheter within steering channel 1360 at attachment 1378, which is near the distal tip of the delivery catheter (not shown). Distal end 1386 of steering wire 1380 is attached to the wall of the tube of the delivery catheter within steering channel 1360 at attachment 1388, which is near the distal tip of the delivery catheter (not shown). Attachment 1378 and attachment 1388 are located on opposing sides of steering channel 1360 such that steering wires 1370 and 1380, when tightened (as explained below), would tend to deflect the delivery catheter in opposite directions. Distal end 1396 of steering wire 1390 is attached to the wall of the tube of the delivery catheter within steering channel 1360 at attachment 1398, which is located on the delivery catheter at a point closer to the proximal end of the delivery catheter than attachments 1378 and 1388. Attachment 1398 is located on the same side of steering channel 1360 as attachment 1388, such that steering wires 1380 and 1390, when tightened (as explained below), would tend to deflect the delivery catheter in the same direction. However, because attachment 1398 is closer to the proximal end of the delivery catheter than is attachment 1388, the tightening of steering wire 1390 tends to deflect the delivery catheter at a point closer to the proximal end of the delivery catheter than does the tightening of steering wire 1380. Thus, as shown in FIG. 9A, the tightening of steering wire 1390 causes a deflection in the delivery catheter approximately at point 1410. The tightening of steering wire 1380 at the same time causes a further deflection in the delivery catheter approximately at point 1420, as shown in FIG. 9B. The tightening of steering wire 1370, therefore, causes a reverse deflection, returning the delivery catheter to its original position (see FIG. 9C).

Referring again to FIG. 7, elongated tube 1010 further includes lumen 1130 and lumen 1140. Lumen 1130 extends from approximately the proximal end (not shown) of tube 1010 to or near distal end 1025 of tube 1010. Lumen 1130 has a bend 1134, relative to tube 1010, at or near distal end 1025 of tube 1010 and an outlet 1136 through wall 1020 of tube 1010 at or near distal end 1025 of tube 1010. Similarly, lumen 1140 has a bend 1144, relative to tube 1010, at or near distal end 1025 of tube 1010 and an outlet 1146 through wall 1020 of tube 1010 at or near distal end 1025 of tube 1010. In the embodiment shown in FIG. 7, lumen 1130 is configured as a laser Doppler tip, and lumen 1140 is sized to accept a retractable sensing lead 1150 and a pacing lead 1160 having a tip at the distal end of the lead. The fiberoptic laser Doppler tip detects and measures blood flow (by measuring the change in wavelength of light emitted by the tip), which helps the clinician to identify—and then avoid—blood vessels during lead placement. Sensing lead 1150 is designed to detect electrical signals in the heart tissue so that the clinician can avoid placing a pacing lead into electrically nonresponsive tissue, such as scar tissue. Pacing lead 1160 is a screw-type lead for placement onto the cardiac tissue, and its tip, which is an electrode, has a substantially screw-like shape. Pacing lead 1160 is capable of operative attachment to a CRT device (not shown) for heart pacing. Although lead 1160 is used for cardiac pacing, any suitable types of leads may be used with the delivery catheters described herein, including sensing leads.

Each of bend 1134 of lumen 1130 and bend 1144 of lumen 1140 forms an approximately 90-degree angle, which allows respective outlets 1136 and 1146 to face the external surface of the heart as the catheter is maneuvered in the pericardial space. However, other embodiments may have bends forming other angles, smaller or larger than 90-degrees, so long as the lumen provides proper access to the external surface of the heart from the pericardial space. Such angles may range, for example, from about 25-degrees to about 155-degrees. In addition to delivering leads and Doppler tips, lumen 1130 and lumen 1140 may be configured to allow, for example, the taking of a cardiac biopsy, the delivery of gene cell treatment or pharmacological agents, the delivery of biological glue for ventricular reinforcement, implementation of ventricular epicardial suction in the acute myocardial infarction and border zone area, the removal of fluid in treatment of pericardial effusion or cardiac tamponade, or the ablation of cardiac tissue in treatment of atrial fibrillation.

For example, lumen 1130 could be used to deliver a catheter needle for intramyocardial injection of gene cells, stems, biomaterials, growth factors (such as cytokinase, fibroblast growth factor, or vascular endothelial growth factor) and/or biodegradable synthetic polymers, RGD-liposome biologic glue, or any other suitable drug or substance for treatment or diagnosis. For example, suitable biodegradable synthetic polymer may include polylactides, polyglycolides, polycaprolactones, polyanhydrides, polyamides, and polyurethanes. In certain embodiments, the substance comprises a tissue inhibitor, such as a metalloproteinase (e.g., metalloproteinase 1).

The injection of certain substances (such as biopolymers and RGD-liposome biologic glue) is useful in the treatment of chronic heart failure to reinforce and strengthen the left ventricular wall. Thus, using the embodiments disclosed herein, the injection of such substances into the cardiac tissue from the pericardial space alleviates the problems and risks associated with delivery via the transthoracic approach. For instance, once the distal end of the delivery catheter is advanced to the pericardial space, as disclosed herein, a needle is extended through a lumen of the delivery catheter into the cardiac tissue and the substance is injected through the needle into the cardiac tissue.

The delivery of substances into the cardiac tissue from the pericardial space can be facilitated using a laser Doppler tip. For example, when treating ventricular wall thinning, the laser Doppler tip located in lumen 1140 of the embodiment shown in FIG. 7 can be used to measure the thickness of the left ventricular wall during the procedure (in real time) to determine the appropriate target area for injection.

Figure 10:
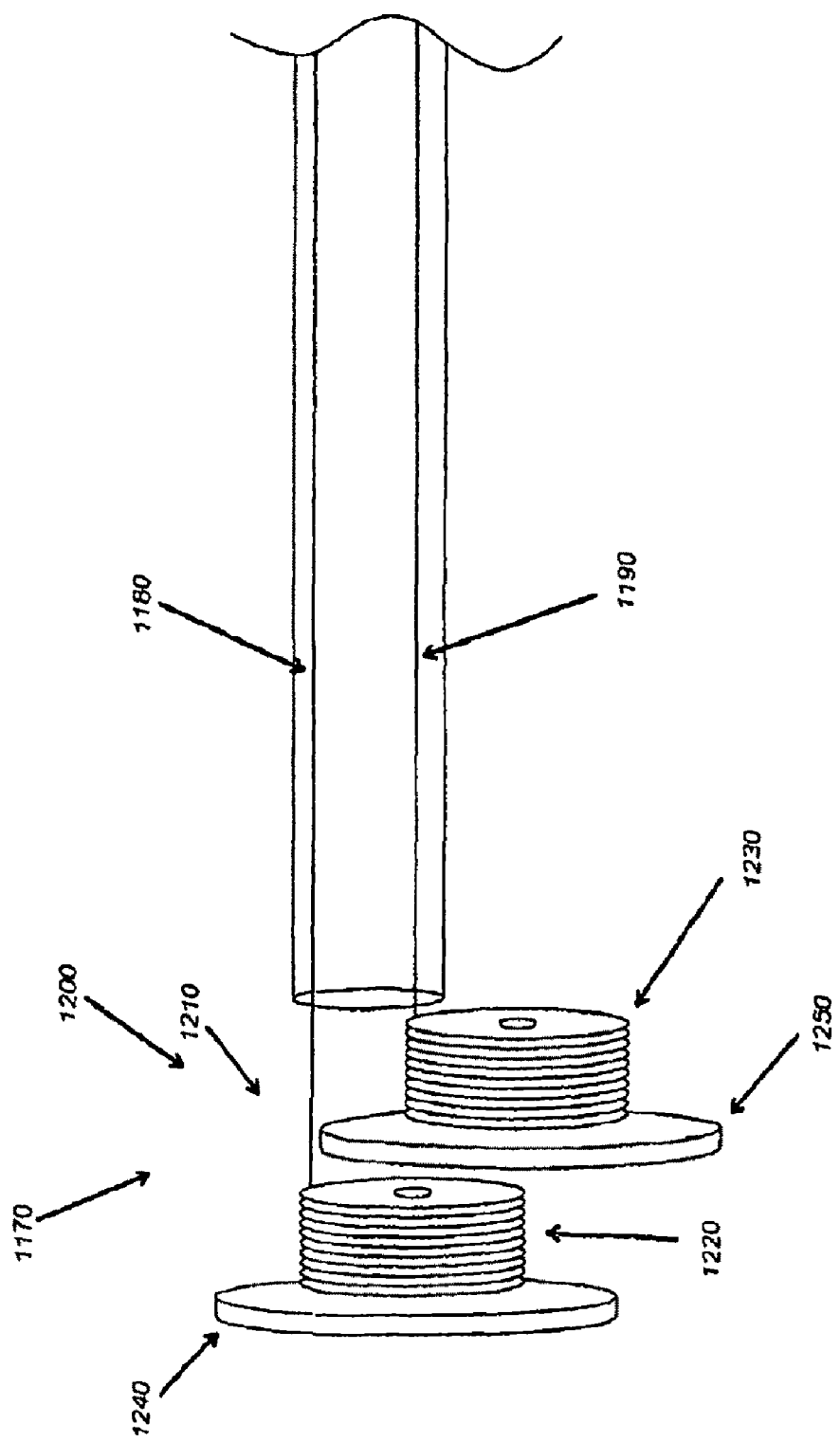
FIG. 10 shows a portion of another embodiment of a steering wire system.

Referring again to FIG. 8, although controller 1080 comprises first handle 1090 and second handle 1094, other embodiments of the controller may include different configurations. For example, instead of using handles, a controller may include any suitable torque system for controlling the steering wires of the steering wire system. Referring now to FIG. 10, there is shown a portion of a steering wire system 1170 having steering wire 1180, steering wire 1190, and controller 1200. Controller 1200 comprises a torque system 1210 having a first rotatable spool 1220, which is capable of collecting and dispensing steering wire 1180 upon rotation. For example, when first rotatable spool 1220 rotates in a certain direction, steering wire 1180 is collected onto spool 1220, thereby tightening steering wire 1180. When spool 1220 rotates in the opposite direction, steering wire 1180 is dispensed from spool 1220, thereby loosening steering wire 1180. Torque system 1210 also has a second rotatable spool 1230, which is capable of collecting and dispensing steering wire 1190 upon rotation, as described above.

Torque system 1210 further includes a first rotatable dial 1240 and a second rotatable dial 1250. First rotatable dial 1240 is attached to first rotatable spool 1220 such that rotation of first rotatable dial 1240 causes rotation of first rotatable spool 1220. Similarly, second rotatable dial 1250 is attached to second rotatable spool 1230 such that rotation of second rotatable dial 1250 causes rotation of second rotatable spool 1230. For ease of manipulation of the catheter, torque system 1210, and specifically first and second rotatable dials 1240 and 1250, may optionally be positioned on a catheter handle (not shown) at the proximal end of tube 1010.

Steering wire system 1170 can be used to direct a delivery catheter through the body in a similar fashion as steering wire system 1140. Thus, for example, when first rotatable dial 1240 is rotated in a first direction (e.g., clockwise), steering wire 1180 is tightened and the delivery catheter is deflected in a certain direction. When first rotatable dial 1240 is rotated in the other direction (e.g., counterclockwise), steering wire 1180 is loosened and the delivery catheter straightens to its original position. When second rotatable dial 1250 is rotated in one direction (e.g., counterclockwise), steering wire 1190 is tightened and the delivery catheter is deflected in a direction opposite of the first deflection. When second rotatable dial 1250 is rotated in the other direction (e.g., clockwise), steering wire 1190 is loosened and the delivery catheter is straightened to its original position.

Certain other embodiments of steering wire system may comprise other types of torque system, so long as the torque system permits the clinician to reliably tighten and loosen the various steering wires. The magnitude of tightening and loosening of each steering wire should be controllable by the torque system.

Referring again to FIG. 11, there is shown a cross-sectional view of delivery catheter 1260. Delivery catheter 1260 includes tube 1265, a first lumen 1270, a second lumen 1280, and a steering channel 1290. Steering wires 1292, 1294, and 1296 are shown within steering channel 1290. First lumen 1270 has outlet 1275, which can be used to deliver a microcamera system (not shown) or a laser Doppler tip 1278. Second lumen 1280 is sized to deliver a pacing lead 1300, as well as a sensing lead (not shown).

A pacing lead may be placed on the external surface of the heart using an engagement catheter and a delivery catheter as disclosed herein. For example, an elongated tube of an engagement catheter is extended into a blood vessel so that the distal end of the tube is in contact with a targeted tissue on the interior of a wall of the heart. As explained above, the targeted tissue may be on the interior of the atrial wall or the atrial appendage. Suction is initiated to aspirate a portion of the targeted tissue to retract the cardiac wall away from the pericardial sac that surrounds the heart, thereby enlarging a pericardial space between the pericardial sac and the cardiac wall. A needle is then inserted through a lumen of the tube and advanced to the heart. The needle is inserted into the targeted tissue, causing a perforation of the targeted tissue. The distal end of a guide wire is inserted through the needle into the pericardial space to secure the point of entry through the cardiac wall. The needle is then withdrawn from the targeted tissue.

A delivery catheter, as described herein, is inserted into the lumen of the tube of the engagement catheter and over the guide wire. The delivery catheter may be a 14 Fr. radiopaque steering catheter. The distal end of the delivery catheter is advanced over the guide wire through the targeted tissue into the pericardial space. Once in the pericardial space, the delivery catheter is directed using a steering wire system as disclosed herein. In addition, a micro-camera system may be extended through the lumen of the delivery catheter to assist in the direction of the delivery catheter to the desired location in the pericardial space. Micro-camera systems suitable for use with the delivery catheter are well-known in the art. Further, a laser Doppler system may be extended through the lumen of the delivery catheter to assist in the direction of the delivery catheter. The delivery catheter is positioned such that the outlet of one of the lumens of the delivery catheter is adjacent to the external surface of the heart (e.g., the external surface of an atrium or a ventricle). A pacing lead is extended through the lumen of the delivery catheter onto the external surface of the heart. The pacing lead may be attached to the external surface of the heart, for example, by screwing the lead into the cardiac tissue. In addition, the pacing lead may be placed deeper into the cardiac tissue, for example in the subendocardial tissue, by screwing the lead further into the tissue. After the lead is placed in the proper position, the delivery catheter is withdrawn from the pericardial space and the body. The guide wire is withdrawn from the pericardial space and the body, and the engagement catheter is withdrawn from the body.

The disclosed embodiments can be used for subendocardial, as well as epicardial, pacing. While the placement of the leads is epicardial, the leads can be configured to have a long screw-like tip that reaches near the subendocardial wall. The tip of the lead can be made to be conducting and stimulatory to provide the pacing to the subendocardial region. In general, the lead length can be selected to pace transmurally at any site through the thickness of the heart wall. Those of skill in the art can decide whether epicardial, subendocardial, or some transmural location stimulation of the muscle is best for the patient in question.

While various embodiments of devices, systems, and methods for accessing the heart tissue have been described in considerable detail herein, the embodiments are merely offered by way of non-limiting examples of the invention described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

We claim:

1. A system for use with a vacuum source for placing a lead into a tissue of a heart, comprising:
    an engagement catheter comprising a proximal end, a distal end, and first and second lumens extending between the proximal end and the distal end;
    a delivery catheter comprising an elongated tube having a wall and a first lumen, wherein the delivery catheter is configured such that the delivery catheter is capable of at least partial insertion into the second lumen of the engagement catheter;
    a lead having a tip at a distal end, the lead configured for at least partial insertion into the first lumen of the delivery catheter; and
    a vacuum port located at the proximal end of the engagement catheter, the vacuum port being operatively connected to the first lumen of the engagement catheter and capable of operative connection to a vacuum source;
    wherein the first lumen of the engagement catheter includes a suction port located at or near the distal end of the engagement catheter, the suction port being configured to removably attach to a targeted tissue on an interior of a wall of a heart after the engagement catheter has been advanced through a blood vessel into the heart, such that the suction port is capable of forming a reversible seal with the targeted tissue when the vacuum source is operatively attached to the vacuum port.

2. The system of claim 1, wherein:
    the first lumen of the delivery catheter extends from approximately the proximal end of the tube to or near the distal end of the tube, the first lumen of the delivery catheter having a bend, relative to the tube, at or near the distal end of the tube and an outlet through the wall of the tube at or near the distal end of the tube.

3. The system of claim 2, wherein:
    the bend of the first lumen of the delivery catheter forms an angle that is approximately 90-degrees.

4. The system of claim 2, wherein:
    the delivery catheter further comprises a second lumen extending from approximately the proximal end of the tube to or near the distal end of the tube, the second lumen of the delivery catheter having a bend, relative to the tube, at or near the distal end of the tube and an outlet through the wall of the tube at or near the distal end of the tube.

5. The system of claim 4, wherein:
    the bend of the first lumen of the delivery catheter forms an angle that is approximately 90-degrees, wherein the bend of the first lumen facilitates delivery of the lead to an external surface of the heart when at least part of the delivery catheter is positioned within a pericardial space; and the bend of the second lumen of the delivery catheter forms an angle that is approximately 90-degrees.

6. The system of claim 2, wherein:

the lead comprises a pacing lead; and the tip of the pacing lead has a substantially screw-like shape.

7. The system of claim 1, wherein:

the delivery catheter further comprises a steering channel extending from a proximal end of the tube to a distal end of the tube and a steering wire system at least partially located in the steering channel; and the steering wire system comprises a first steering wire, a second steering wire, and a controller, each of the first and second steering wires being attached to the wall of the tube within the steering channel and the controller being attached to a proximal end of each of the first and second steering wires.

8. The system of claim 7, wherein:

the controller of the steering wire system comprises a first handle attached to the proximal end of the first steering wire and a second handle attached to the proximal end of the second steering wire.

9. The system of claim 7, wherein:

the controller of the steering wire system comprises a torque system having a first rotatable spool capable of collecting and dispensing the first steering wire and a second rotatable spool capable of collecting and dispensing the second steering wire.

10. The system of claim 7, wherein:

the steering wire system further comprises a third steering wire;

the first steering wire is attached to the wall of the tube within the steering channel at the distal end of the tube, the attachment between the first steering wire and the wall forming a first attachment point;

the second steering wire is attached to the wall of the tube within the steering channel at the distal end of the tube, the attachment between the second steering wire and the wall forming a second attachment point;

the third steering wire is attached to the wall of the tube within the steering channel at the distal end of the tube, the attachment between the third steering wire and the wall forming a third attachment point; and the third attachment point is closer to the proximal end of the tube than is the first attachment point or the second attachment point.

11. The system of claim 7, wherein:

the delivery catheter further comprises a handle at or near the proximal end of the tube; and the controller of the steering wire system is attached to the handle.

12. A method of placing a lead in a tissue of a heart, the method comprising:

extending into a blood vessel an elongated tube having a proximal end, a distal end, and a first lumen, such that the distal end of the tube is in contact with a targeted tissue on an interior of a wall of a heart;

aspirating the targeted tissue such that the wall of the heart is retracted away from a pericardial sac surrounding the heart to enlarge a pericardial space between the pericardial sac and the wall of the heart;

accessing the pericardial space through the targeted tissue;

inserting into the first lumen of the elongated tube and over an elongated guide wire a delivery catheter comprising a first lumen, wherein the first lumen of the delivery catheter has a bend at or near the distal end of the delivery catheter to facilitate delivery of a lead into a tissue of the heart when at least part of the delivery catheter is positioned within the pericardial space and an outlet at or near the distal end of the delivery catheter;

advancing at least the distal end of the delivery catheter through the targeted tissue into the pericardial space;

directing the delivery catheter such that the outlet of the first lumen of the delivery catheter is adjacent to the tissue of the heart; and extending a lead through the first lumen of the delivery catheter into the tissue of the heart.

13. The method of claim 12, wherein:

the delivery catheter further comprises a steering channel and a steering wire system located at least partially within the steering channel; and the step of directing the delivery catheter such that the outlet of the first lumen of the delivery catheter is adjacent to the tissue of the heart comprises directing the delivery catheter with the steering wire system.

14. The method of claim 13, further comprising:

extending a laser Doppler tip through a second lumen of the delivery catheter to the pericardial space.

15. The method of claim 13, wherein:

the lead is a pacing lead; and the steering wire system further comprises at least two steering wires attached to the delivery catheter inside the steering channel and a controller attached to the proximal ends of the at least two steering wires, the controller being capable of collecting and dispensing at least one of the at least two steering wires.

16. The method of claim 15, wherein:

the step of directing the delivery catheter using the steering wire system comprises using the controller to tighten at least one of the at least two steering wires.

17. The method of claim 16, further comprising:

inserting into the targeted tissue over the elongated guide wire a plug having a first end, a second end, and a hole extending from the first end to the second end, wherein the hole of the plug is self-sealing after removal of the guide wire.

18. A method of injecting a substance into a cardiac tissue from the pericardial space surrounding the external surface of a heart, the method comprising:

extending into a blood vessel an elongated tube having a proximal end, a distal end, and a first lumen, such that the distal end of the tube is in contact with a targeted tissue on an interior of a wall of a heart;

aspirating the targeted tissue such that the wall of the heart is retracted away from a pericardial sac surrounding the heart to enlarge a pericardial space between the pericardial sac and the wall of the heart;

accessing the pericardial space through the targeted tissue;

inserting at least the distal end of an elongated guide wire into the pericardial space;

inserting into the first lumen of the elongated tube and over the elongated guide wire a delivery catheter comprising a first lumen, wherein the first lumen of the delivery catheter has a bend at or near the distal end of the delivery catheter to facilitate injection of a substance into a cardiac tissue when at least part of the delivery catheter is positioned within the pericardial space and an outlet at or near the distal end of the delivery catheter;

advancing at least the distal end of the delivery catheter through the targeted tissue into the pericardial space;

directing the delivery catheter such that the outlet of the first lumen of the delivery catheter is adjacent to the external surface of the heart;

extending a needle through the first lumen of the delivery catheter into the cardiac tissue; and injecting the substance into the cardiac tissue.

19. The method of claim 18, wherein:
the substance is selected from the group consisting of gene cells, growth factors, a biodegradable synthetic polymer, a tissue inhibitor, a metalloproteinase, and RGD-liposome biologic glue.

20. The method of claim 18, wherein:
the substance comprises a biodegradable synthetic polymer selected from the group consisting of polylactides, polyglycolides, polycaprolactones, polyanhydrides, polyamides, and polyurethanes.

21. The method of claim 18, wherein:
the substance comprises a tissue inhibitor comprising a metalloproteinase.

22. The method of claim 18, wherein:
the delivery catheter further comprises a second lumen, wherein the second lumen of the delivery catheter has a bend at or near the distal end of the delivery catheter and an outlet at or near the distal end of the delivery catheter.

23. The method of claim 22, wherein:
the delivery catheter further comprises a laser Doppler tip.

24. The method of claim 23, further comprising the step of:
measuring the thickness of the cardiac tissue using the laser Doppler tip.

25. The system of claim 1, wherein the system is capable of enlarging a pericardial space between the targeted tissue and a pericardial sac that surrounds the heart by retracting the targeted tissue away from the pericardial sac.

* * * * *